(12) United States Patent
Criscione et al.

(10) Patent No.: US 7,935,045 B2
(45) Date of Patent: May 3, 2011

(54) DEVICE FOR PROACTIVE MODULATION OF CARDIAC STRAIN PATTERNS

(75) Inventors: John C. Criscione, College Station, TX (US); Lewis Harrison, Arlington, TX (US)

(73) Assignees: The Texas A&M University System, College State, TX (US); Corinnova Incorporated, College Station, TX (US)

( * ) Notice: Subject to any disclaimer, the term of this patent is extended or adjusted under 35 U.S.C. 154(b) by 871 days.

(21) Appl. No.: 11/400,148

(22) Filed: Apr. 6, 2006

(65) Prior Publication Data
US 2007/0260108 A1    Nov. 8, 2007

Related U.S. Application Data

(60) Provisional application No. 60/668,640, filed on Apr. 6, 2005.

(51) Int. Cl.
*A61N 1/362* (2006.01)
(52) U.S. Cl. .................................................... 600/16
(58) Field of Classification Search ............ 600/16, 600/17, 37; 601/153; 623/3
See application file for complete search history.

(56) References Cited

U.S. PATENT DOCUMENTS

| | | | |
|---|---|---|---|
| 2,826,193 A | 3/1958 | Vineberg | |
| 3,034,501 A | 5/1962 | Hewson | |
| 3,233,607 A | 2/1966 | Bolie | |
| 3,513,836 A | 5/1970 | Sausse | |
| 4,048,990 A * | 9/1977 | Goetz | 601/153 |
| 4,536,893 A | 8/1985 | Parravicini | |
| 5,119,804 A | 6/1992 | Anstadt | |
| 5,256,132 A * | 10/1993 | Snyders | 600/16 |
| 5,749,839 A * | 5/1998 | Kovacs | 601/153 |
| 5,863,574 A | 1/1999 | Julien | |
| 6,224,540 B1 | 5/2001 | Lederman et al. | |
| 6,387,042 B1 * | 5/2002 | Herrero | 600/37 |
| 6,540,666 B1 | 4/2003 | Chekanov | |
| 6,592,619 B2 | 7/2003 | Melvin | |
| 6,595,912 B2 | 7/2003 | Lau et al. | |
| 6,602,182 B1 | 8/2003 | Milbocker | |
| 6,602,184 B2 | 8/2003 | Lau et al. | |
| 6,612,978 B2 | 9/2003 | Lau et al. | |
| 6,612,979 B2 | 9/2003 | Lau et al. | |

(Continued)

FOREIGN PATENT DOCUMENTS

WO     99/22784     5/1999

OTHER PUBLICATIONS

International Search Report and Written Opinion for PCT/US2005/003343 dated Jul. 16, 2007.

(Continued)

*Primary Examiner* — Carl H Layno
*Assistant Examiner* — Brian T Gedeon
(74) *Attorney, Agent, or Firm* — Chainey P. Singleton; Chalker Flores, LLP

(57) ABSTRACT

The present invention provides methods, systems and devices that reduce dyskinesis and hypokinesis. The contoured heart assist device of the present invention includes a selectively inflatable end-systolic heart shaped bladder with one or more contoured supports configured to surround at least a portion of the heart and provide curvatures similar to the proper shape of the heart when the device is pressurized and one or more fluid connections in communication with the selectively inflatable end-systolic heart shaped bladder for pressurization and depressurization.

20 Claims, 15 Drawing Sheets

U.S. PATENT DOCUMENTS

| | | |
|---|---|---|
| 6,663,558 B2 | 12/2003 | Lau et al. |
| 6,784,283 B2 | 8/2004 | Anderson et al. |
| 7,445,593 B2 | 11/2008 | Criscione |
| 7,494,459 B2 | 2/2009 | Anstadt et al. |
| 2002/0065449 A1 | 5/2002 | Wardle |

OTHER PUBLICATIONS

Anstadt, M.P., et al., "Non-blood contacting biventricular support for severe heart failure." Ann Thorac Surg (2002), 73:556-62.

Artrip, J.H., et al., "Physiological and hemodynamic evaluation of nonuniform direct cardiac compression." Circulation (1999), 100(suppl II):236-43.

Cohn, J. N., "Cardiac Remodeling—Concepts and Clinical Implications: A Consensus Paper from an International Forum on Cardiac Remodeling," Journal of American College of Cardiology (2000), 35(3):569-582.

Dipla, K., et al., "Myocyte recovery after mechanical circulatory support in humans with end-stage heart failure." Circulation (1998), 97:2316-2322.

Goldstein, D.J., et al., "Medical progress: implantable left ventricular assist devices." N Engl J Med (1998), 339 (21):1522-1533.

Heerdt, P.M., et al., "Chronic unloading by left ventricular assist device reverses contractile dysfunction and alters gene expression in end-stage heart failure." Circulation (2000), 102:2713-2719.

Karvarana, M.N., et al., "Circulatory support with a direct cardiac compression device: a less invasive approach with the AbioBooster device." J Thorac Cardiovasc Surg (2001), 122:786-787.

Kawaguchi, O., et al., "Mechanical enhancement of myocardial oxygen saving by synchronized dynamic left ventricular compression." J Thorac Cardiovasc Surg (1992), 103:573-81 (Abstract).

Kherani, A.R., et al., "Ventricular assist devices as a bridge to transplant or recovery." Cardiol (2004), 101:93-103.

Omens, J.H. "Stress and strain as regulators of myocardial growth." Prog. Biophys. Molec. Biol. (1998), 69:559-572.

Oz, M.C., et al., "Direct cardiac compression devices." J Heart Lung Transplant (2002), 21:1049-1055.

Rose, E.A., et al., "Long-term use of left ventricular assist device for end-stage heart failure." N Engl J Med (2001), 345(20):1435-1443.

Williams, M.R., and Artrip, J.H. "Direct cardiac compression for cardiogenic shock with the CardioSupport System." Ann Thorac Surg (2001), 71:S188-9.

International Search Report and Written Opinion for PCT/US2008/071618 dated Feb. 12, 2009.

* cited by examiner

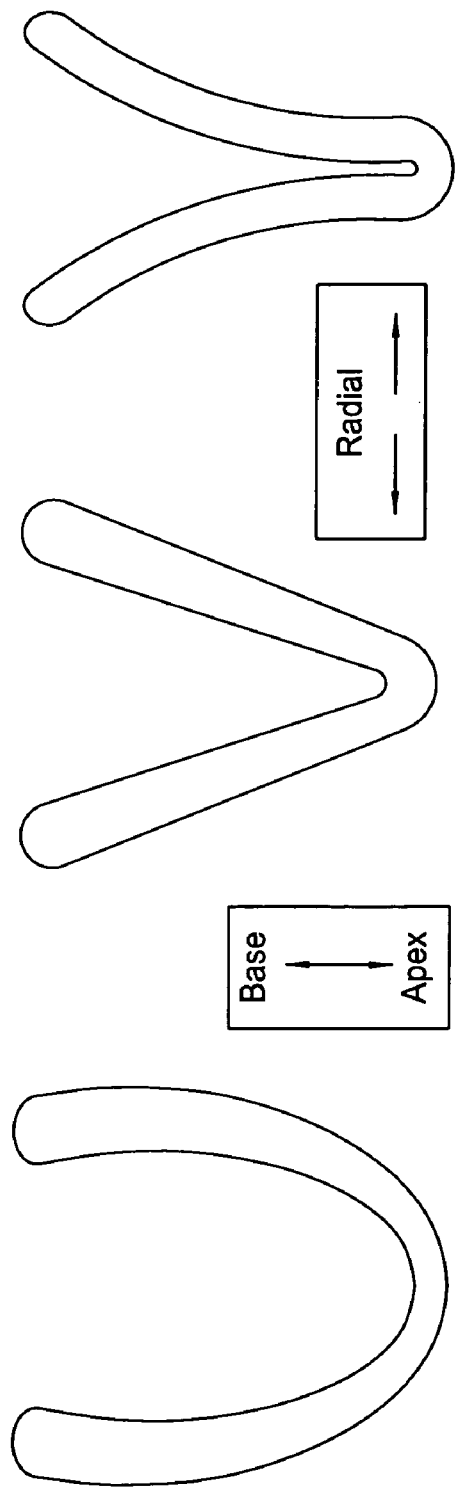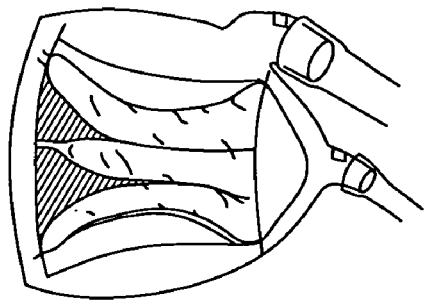
FIG. 2C
FIG. 2B
FIG. 2A
FIG. 2D

FIG. 14
FIG. 15
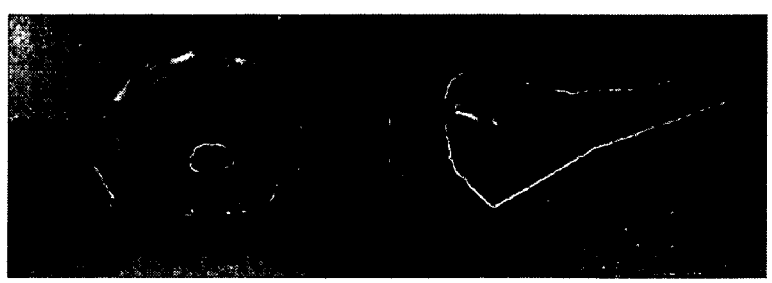

DEVICE FOR PROACTIVE MODULATION OF CARDIAC STRAIN PATTERNS

CROSS-REFERENCE TO RELATED APPLICATIONS

This application claims priority to U.S. Provisional Application Ser. No. 60/668,640, filed Apr. 6, 2005, and is related to U.S. patent application Ser. No. 10/870,619, filed Jun. 17, 2004, the contents of each is incorporated by reference herein in its entireties.

This invention was made with U.S. Government support under the Department of Health and Human Services, National Institutes of Health, NATIONAL HEART, LUNG, AND BLOOD INSTITUTE, Grant Number: 4 R42 HL080759-02. The government has certain rights in this invention.

TECHNICAL FIELD OF THE INVENTION

The present invention relates in general to a mechanical interface for the heart of a patient to improve its pumping function, and more particularly, modulating contraction strain patterns on a diseased or damaged heart in order to reduce dyskinetic or hypokinetic motions.

BACKGROUND OF THE INVENTION

Congestive heart failure affects an estimated 5 million people and results in an estimated $28.8 billion dollars being spent on health care relating to congestive heart failure (see AHA, 2003). As a result congestive heart failure treatments have become a substantial research interest.

Pharmacotherapy is minimally invasive and is a preferred form of treatment for congestive heart failure; however, pharmacotherapy has risks. Additionally, pharmacotherapy can be ineffective for mechanical problems, such that surgical intervention is necessary. For example, cardiovascular diseases with aberrant growth and remodeling may be in the class of diseases with a mechanical etiology, because it is now evident that local mechanical stimuli are major controllers of growth and remodeling in cardiovascular tissues. As the heart functions to produce mechanical work, mechanical strain may be one of the primary stimuli in cardiac development and adaptation.

For example, a recent publication (Rose et al., 2001) examined the Randomized Evaluation of Mechanical Assistance for the Treatment ("REMATCH trial") of congestive heart failure ("CHF"). The REMATCH trial was a major, multicenter (20), large trial (129 patients) designed to compare long-term cardiac assist treatments to pharmacological treatment in the areas of survival, serious adverse events, number of days of hospitalization and quality of life. The REMATCH trial states, "Patients with mild-to-moderate heart failure [SOLVD, 1991] and, recently, some with more severe disease [Packer et al., 2001] have been shown to benefit from drug therapy. Nevertheless, the survival and the quality of life of patients with severe heart failure remain limited. Cardiac transplantation is the only treatment that provides substantial individual benefit, but with fewer than 3,000 donor hearts available worldwide per year, its impact is epidemiologically trivial [Hosenpud et al., 2000]."

Despite having an increased number of adverse events and hospitalizations, the group with mechanical assist had a significantly higher survival rate and quality of life. The success of the REMATCH trial contributed to the recent action of the FDA to approve cardiac assist devices for use in end-stage heart failure patients who are not waiting for a transplant. Prior to this, cardiac assist devices were only approved as a bridge to transplantation.

One heart assist device is shown in U.S. Pat. No. 5,119,804, issued on Jun. 9, 1992 to Anstadt, for a cardiac massage apparatus and a drive system. The cardiac massage apparatus includes a cup having a liner that is connected within the cup at its upper and lower ends. Dimensions defining an optimum cup shape as a function of ventricular length are disclosed wherein the heart remains within the cup when mechanically activated.

Other examples include U.S. Pat. Nos. 6,663,558; 6,612,979; 6,612,978; 6,602,184 and 6,595,912 issued to Lau, et al., for a cardiac harness to treat congestive heart failure. The harness applies elastic, compressive reinforcement on the left ventricle to reduce deleterious wall tension and to resist shape change of the ventricle during the mechanical cardiac cycle. Rather than imposing a dimension beyond which the heart cannot expand, the harness provides no hard limit over the range of diastolic expansion of the ventricle. Instead, the harness follows the contour of the heart throughout diastole and continuously exerts gentle resistance to stretch.

U.S. Pat. No. 6,602,182, issued Aug. 5, 2003 to Milbocker, for a unified, non-blood contacting, implantable heart assist system surrounds the natural heart and provides circumferential contraction in synchrony with the heart's natural contractions. The pumping unit includes adjacent tube pairs arranged along a bias with respect to the axis of the heart and bound in a non-distensible sheath forming a heart wrap. The tube pairs are tapered at both ends such that when they are juxtaposed and deflated they approximately follow the surface of the diastolic myocardium. Inflation of the tube pairs causes the wrap to follow the motion of the myocardial surface during systole. A muscle-driven or electromagnetically powered energy converter inflates the tubes using hydraulic fluid pressure. An implanted electronic controller detects electrical activity in the natural heart, synchronizes pumping activity with this signal, and measures and diagnoses system as well as physiological operating parameters for automated operation. A transcutaneous energy transmission and telemetry subsystem allows the Unified System to be controlled and powered externally.

U.S. Pat. No. 6,592,619, issued on Jul. 15, 2003 to Melvin, for an actuation system for assisting the operation of the natural heart. The system includes a framework for interfacing with a natural heart, through the wall of the heart, which includes an internal framework element configured to be positioned within the interior volume of a heart and an external framework element configured to be positioned proximate an exterior surface of the heart. The internal framework is flexibly suspended with respect to the external frame. An actuator system is coupled to the framework and configured to engage an exterior surface of the heart. The actuator system includes an actuator band extending along a portion of a heart wall exterior surface. The actuator band is selectively movable between an actuated state and a relaxed state and is operable, when in the actuated state, to assume a predetermined shape and thereby indent a portion of the heart wall to affect a reduction in the volume of the heart. A drive apparatus is coupled to the actuator band and is operable for selectively moving the actuator band between the relaxed and actuated states to achieve the desired assistance of the natural heart.

U.S. Pat. No. 6,224,540 issued on May 1, 2001 to Lederman, et al., relates to a passive girdle for heart ventricle for therapeutic aid to patients having ventricular dilatation. A passive girdle is wrapped around a heart muscle which has dilatation of a ventricle to conform to the size and shape of the heart and to constrain the dilatation during diastole. The girdle is formed of a material and structure that does not expand away from the heart but may, over an extended period of time be decreased in size as dilatation decreases.

The foregoing problems have been recognized for many years and while numerous solutions have been proposed, none of them adequately address all of the problems.

SUMMARY OF THE INVENTION

The present inventors recognized that strain is a primary controller of myocardial growth, remodeling, and recovery. The present inventors also recognized pharmacotherapy does not eliminate aberrant motion, e.g., through indirect control of strain via such mechanisms as afterload reduction. The present inventors recognized that a device, a system, a method and a kit are needed that eliminate aberrant strain patterns and once normal cardiac kinematics are restored the heart may be weaned from the device.

The present invention relates to an inflatable end-systolic heart shaped bladder and methods of implanting, using and removing such a device. The present invention provides a contoured heart assist device that reduces dyskinesis and hypokinesis. The device includes a selectively inflatable end-systolic heart shaped bladder with one or more contoured supports configured to surround at least a portion of the heart to provide curvatures similar to the proper shape of the heart when pressurized. One or more fluid connections are in communication with the selectively inflatable end-systolic heart shaped bladder for pressurization and depressurization.

The present invention also provides a contoured direct cardiac compression device that applies forces to the exterior epicardial boundary of the heart to restrict inflow and modulate right flow versus left flow through the heart. The contoured direct cardiac compression device includes a selectively inflatable end-diastolic contoured bladder, an inlet connection and an outlet connection. The selectively inflatable end-diastolic contoured bladder includes one or more contoured supports, configured to engage releasably the heart. The one or more contoured supports protrude inward towards the right ventricle to decrease the end-diastolic volume of the right ventricle during diastole.

The present invention provides a method for promoting growth and remodeling the heart. A selectively inflatable end-systolic heart shaped bladder is positioned about at least a portion of the periphery of the heart of a patient. A fluid source that is connected to the selectively inflatable end-systolic heart shaped bladder, that inflates with a positive pressure during systole and deflates the selectively inflatable end-systolic heart shaped bladder during diastole is activated.

The present invention also provides a direct cardiac compression device that promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

The present invention provides a direct cardiac compression device that applies forces to the exterior epicardial boundary of the heart and is optimized to fit an end-systolic shaped heart geometry. The device includes 2 or more contoured compartments, an inlet connection and an outlet connection. The 2 or more contoured compartments are configured to surround at least a portion of the heart and individually contoured to provide curvatures that are similar to the proper end-systolic shape of the heart when pressurized. The inlet connection is in communication with the 2 or more inflatable contoured compartments and an outlet connection in communication with the 2 or more inflatable contoured compartments.

The present invention also provides a method of reshaping the heart muscle of a patient by providing a direct cardiac compression device that compresses the heart during contraction without inverting or significantly perturbing the curvatures of the heart. A selectively inflatable end-systolic heart shaped bladder is positioned about at least a portion of the periphery of the heart once access is made to the heart of the patient. The next step is the connecting of a fluid source to the selectively inflatable end-systolic heart shaped bladder to inflate with a positive pressure during systole and deflate the selectively inflatable bladder during diastole.

The present invention relates to a soft shell direct cardiac compression device and methods of implanting, using and removing such a device. In one embodiment, the invention relates to a direct cardiac compression device that surrounds the heart and includes a soft shell and a compression mechanism. The compression mechanism is operable to actively promote a contraction strain pattern on a diseased or damaged myocardium that promotes beneficial growth and remodeling of the myocardium. More particularly, the contraction strain pattern may be characterized by non-inversion or lack of gross perturbation of the heart's curvature. The device may include a plurality of inflatable chambers.

In another embodiment, the invention relates to a direct cardiac compression device having a soft shell and a plurality of inflatable chambers. The device exerts a non curvature-inverting contraction strain pattern when used on a heart. The device may be used on a heart without requiring attachment to the valve plane or other suturing to the heart.

The inflatable chambers may be formed from two sheets of material sealed and connected at a plurality of locations to form the plurality of chambers. The inflatable chambers may be made of a biocompatible material such as polyethylene. The direct cardiac compression device may also include a plurality of stabilizing rods, members or stents. An apical hole may be formed by the apical tips of the inflatable chambers.

The direct cardiac compression device may inflate the chambers in any way practical, but in a particular embodiment, it has at least one pneumatic drive line operable to inflate at least one of the plurality of inflatable chambers. It may include other pneumatic drives operable to inflate separate chambers. In some embodiments, the device may be operable to provide differential pressure to the left ventricle and the right ventricle during diastole when used on a heart.

Yet another embodiment of the invention provides a method of assisting a diseased or damaged heart by providing a soft shell direct cardiac compression device to the heart that compresses the heart during contraction without inverting or significantly perturbing the curvatures of the heart. Such methods include several beneficial effects such as inducing ventricular recovery in the heart, promoting growth and remodeling of the myocardium, and preserving the myocardium in a borderzone of a myocardial infarct.

The method may include implanting or removing the device without opening the chest cavity. Such implantation or removal, more specifically, may occur through a sub-xyphoid incision and/or through a mediastinoscopy procedure. The device may be implanted without suturing to the heart. Additionally, the method may also include gradually decreasing compression of the heart to allow the heart to be weaned from the direct cardiac compression device as it recovers.

In some embodiments, the unpressurized device has a very low structural rigidity such that it can be inserted and implanted through a small, sub-xiphoid incision. Similarly, explantation is minimally invasive and done through an enlargement/combination of driveline tracks. The pressurized device takes on a systolic configuration with normal cardiac curvatures. The induction of this systolic shape proactively modulates the strain pattern and intrinsically draws the heart into the device allowing for minimal sewing or similar attachment to the ventricles or valve plane. Hence, valve plane geometry and thus function are unaltered and implantation is quick and may be performed without cardiopulmonary bypass.

Pneumatic separation of the chambers that abut the RV inflow tract may permit partial impeding of RV filling to compensate for increased RV ejection. Because systolic geometry is not grossly abnormal, the amount of assist may be graded and thus a heart can be gradually weaned from the proposed device. In case of device failure, the default to vacuum on the pneumatic drive lines makes the device floppy and less likely to impede heart function. Additionally, aortic balloon technology that has been in use for 30 years may be used to drive the device of the present invention.

To both implant and explant the assist devices of the present invention, a small thoracotomy is desirable. The unpressurized device has a very low structural rigidity and the soft outer shell allows implantation through a much smaller incision. The device has both diastolic and systolic configurations that produce normal cardiac curvatures.

BRIEF DESCRIPTION OF THE DRAWINGS

For a more complete understanding of the features and advantages of the present invention, reference is now made to the detailed description of the invention along with the accompanying figures and in which:

FIG. 2 is a diagram shows the normal, null and inverted curvature in apex-to-base, radial plane of the heart;

FIG. 6 is a schematic diagram of the cross-section of a device according to one embodiment of the present invention without a heart inside, wherein

FIG. 7 is a schematic diagram of the long-section of a device according to one embodiment of the present invention without a heart inside, wherein

FIG. 8 is a schematic diagram of the cross-section of a device according to one embodiment of the present invention with a heart inside, wherein FIG. 8A is in the deflated state and FIG. 8B is in the pressurized state;

FIG. 9 is a schematic diagram of the long-section of a device according to an embodiment of the present invention with a heart inside, wherein FIG. 9A is in the deflated state and FIG. 9B is in the pressurized state;

FIG. 14 is an image that illustrates a device according to one embodiment of the present invention with an ovine heart inside;

FIG. 15 is an image that illustrates a device according to one embodiment of the present invention;

DETAILED DESCRIPTION OF THE INVENTION

Figure 1:
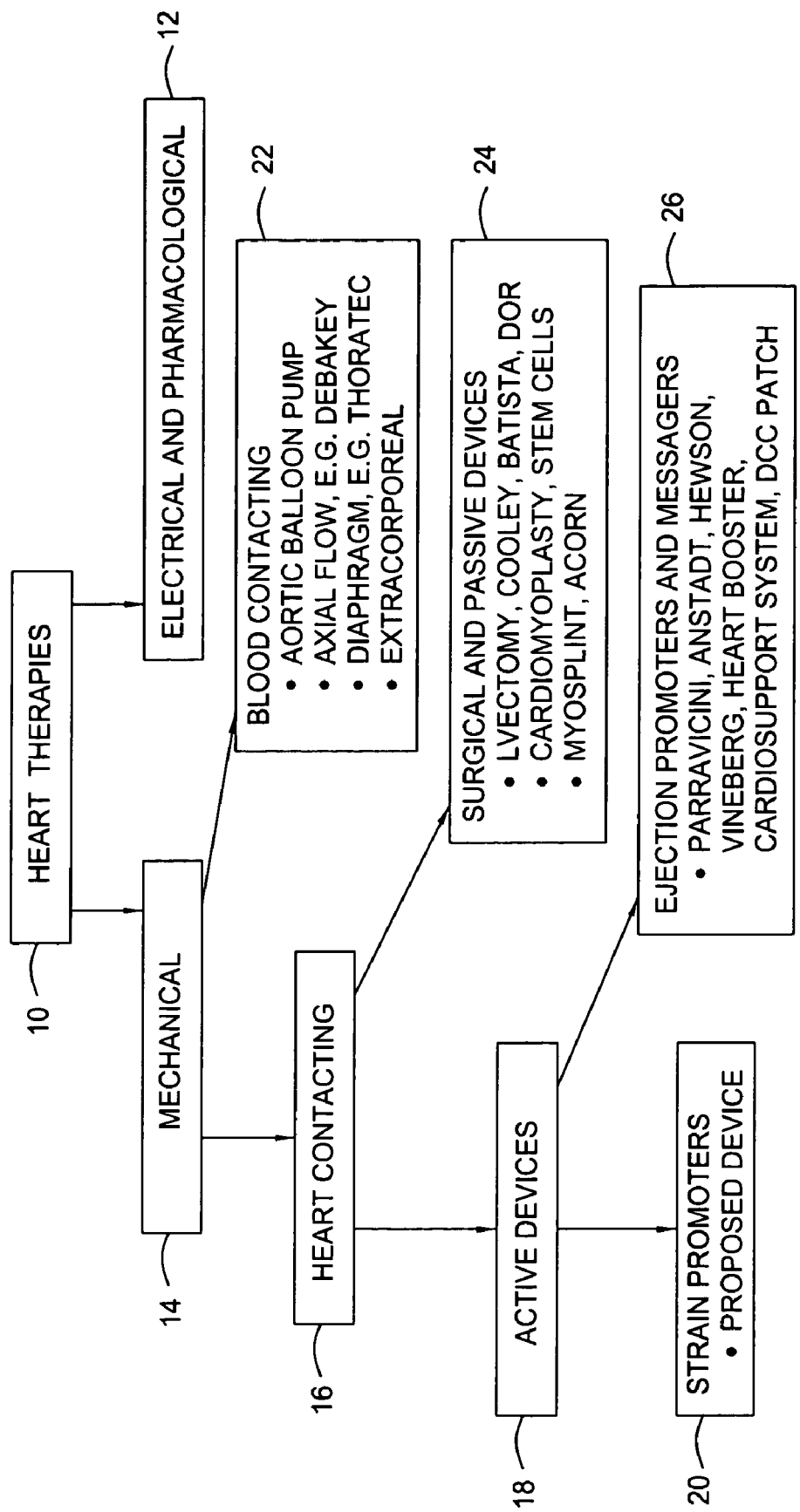
FIG. 1 is a chart that illustrates the classification of heart therapies.

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the "cardiac rekinesis therapy" is the restoration of physiological or beneficial motion to the heart, or in other words, to eliminate aberrant or pathophysiological motions or strains, as opposed to circulatory assist therapies.

As used herein, a "biomedical material" is a material which is physiologically inert to avoid rejection or other negative inflammatory response.

The present invention provides a contoured heart assist device that reduces dyskinesis and hypokinesis. The device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization.

The one or more contoured supports form one or more inflatable compartments having an expanded curvature optimized to fit generally the proper end-systolic shape of the heart. The selectively inflatable end-systolic heart shaped bladder includes an inner membrane that is at least partially folded when depressurized and at least partially unfolded when pressurized. In another embodiment, the selectively inflatable end-systolic heart shaped bladder includes an inner membrane that is at least partially folded when depressurized and at least partially unfolded when pressurized and an outer membrane that is at least partially folded when depressurized and at least partially unfolded when pressurized. Other embodiments may include various combinations thereof.

The one or more contoured supports may include one or more dividers individually of similar or different materials, one or more wires individually of similar or different materials or a combination thereof to form a shape generally appropriate to the proper end-systolic shape of the heart. The selectively inflatable end-systolic heart shaped bladder includes a material that is substantially biocompatible, fluid-impermeable and substantially elastic. For example, at least a portion of the device may be made from elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-ether glycol) urethanes, poly(hexamethylenecarbonate-ethylenecarbonate glycol) urethanes and combinations thereof.

The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more inflatable tapered compartments. Furthermore, the distribution of the inflatable tapered compartments may vary from the design of 4 chambers on the RV side and 8 chambers that are mostly on the LV but also overlapping the interventricular sulci. For example, the device may have 1, 2, 3, 4, 5, 6, 7, 8, 9, 10, 11, 12 or more chambers on the RV side and 1, 2, 3, 4, 5, 6, 7, 8, 9, 10, 11, 12, 13, 14, 15, 16, 17, 18, 19, 20, 21, 22, 23, 24 or more chambers that are mostly on the LV and overlapping the interventricular sulci. That chambers distribution determination for a particular application and treatment is within the scope of the skilled artisan.

The inflatable tapered compartments are connected to a pneumatic pressure source through an inlet port and an outlet port. The device is inflated with a positive pressure during systole and deflated via suction during diastole. Although, other configurations and multiple connections are also possible depending on the particular application and configuration. The inlet port and an outlet port may be connected through a single connection for applying the positive pressure and the suction or negative pressure; alternatively, multiple connections may be used. In addition, the inlet port and an outlet port may be made anywhere about the boundary of the selectively inflatable end-systolic heart shaped bladder, e.g., near the base or near the apex.

The present invention also provides a contoured direct cardiac compression device that applies forces to the exterior, epicardial boundary of the heart to restrict inflow and modulate right flow versus left flow through the heart. The device includes a selectively inflatable end-diastolic contoured bladder having one or more contoured supports configured to releasable engage the heart. The one or more contoured supports protrude inward towards the right ventricle to decrease the end-diastolic volume of the right ventricle during diastole. The device also has an inlet connection and outlet connection in communication with the selectively inflatable end-diastolic contoured bladder to pressurize and depressurize the selectively inflatable end-diastolic contoured bladder. Residual pressure is applied about the right ventricle to not fully deflate during diastole.

Generally, the inlet line is in communication with the inlet connection to operatively expand the selectively inflatable end-diastolic contoured bladder and an outlet line is in communication with the outlet connection to operative withdraw fluid from the selectively inflatable end-diastolic contoured bladder. This allows connection to conventional devices to apply and remove pressure or custom devices specifically for the present invention.

The present invention provides a method for promoting growth and remodeling of the heart. Once access to the heart of the patient is provided, a selectively inflatable end-systolic heart shaped bladder can be positioned about at least a portion of the periphery of the heart.

The selectively inflatable end-systolic heart shaped bladder is then connected to a fluid source to inflate the selectively inflatable end-systolic heart shaped bladder with a positive pressure during systole and deflate the selectively inflatable end-systolic heart shaped bladder during diastole. Alternatively, the selectively inflatable end-systolic heart shaped bladder may be connected to the fluid source before positioning and subsequently activating to inflate and deflate the selectively inflatable end-systolic heart shaped bladder.

The present invention provides a contoured heart device that reduces dyskinesis and hypokinesis having an end-systolic heart contoured bladder with one or more contoured supports configured to surround at least a portion of the heart to provide curvatures that are similar to the proper end-systolic shape of the heart.

A method for promoting growth and remodeling of the heart is provided by the present invention. The method includes providing access to a heart of a patient and positioning a selectively inflatable end-diastolic heart shaped bladder about at least a portion of the periphery of the heart. The selectively inflatable end-diastolic heart shaped bladder is connected to a fluid source to the selectively inflatable end-diastolic heart shaped bladder to inflate with a positive pressure during systole and deflate the selectively inflatable bladder during diastole. The residual pressure is applied about the right ventricle to not fully deflate during diastole.

The selectively inflatable end-diastolic heart shaped bladder includes a pressurizable chamber formed by an inner membrane and an outer membrane and one or more contoured supports positioned within the pressurizable chamber to provide curvatures that are similar to the proper end-diastolic shape of the heart when the pressurizable chamber is pressurized. The one or more end-diastolic contoured supports form one or more inflatable compartments having an expanded curvature optimized to fit the heart geometry similar to the proper end-diastolic shape of the heart.

A direct cardiac compression device that applies forces to the exterior, epicardial boundary of the heart optimized to fit an end-systolic shaped heart geometry is provided by the present invention. The direct cardiac compression device includes a selectively inflatable bladder having one or more end-systolic contoured supports configured to surround at least a portion of the periphery of the heart and provide curvatures similar to the proper end-systolic shape of the heart when the pressurizable chamber is pressurized and one or more fluid connections in communication with the selectively inflatable bladder to pressurize and depressurize the selectively inflatable bladder.

The present invention also provides a direct cardiac compression device that promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

A method of assisting a diseased or damaged heart including providing a direct cardiac compression device that compresses the heart during contraction without inverting or significantly perturbing the curvatures of the heart by positioning a selectively inflatable end-systolic heart shaped bladder about at least a portion of periphery of the heart once access is made to the heart of the patient. The next step is the activating of a fluid source to the selectively inflatable end-systolic heart shaped bladder to inflate with a positive pressure during systole and deflate the selectively inflatable bladder during diastole.

The present invention provides a direct cardiac compression device that applies forces to the exterior, epicardial boundary of the heart optimized to fit an end-systolic shaped heart geometry. The device includes 1 or more contoured compartments, an inlet connection and an outlet connection. The 1 or more contoured compartments are configured to surround at least a portion of the heart and are individually contoured to provide curvatures that are similar to the proper end-systolic shape of the heart when pressurized. The inlet connection is in communication with the 1 or more inflatable contoured compartments and an outlet connection in communication with the 1 or more inflatable contoured compartments. For example, the present invention may be a direct cardiac compression device contoured to surround at least a portion of the heart. The device includes a single chamber with a plurality of structures contained therein that provide support to create the end-systolic shaped heart geometry.

The present invention also provides a dyskinesis and hypokinesis reduction system including a contoured heart assist device and a pressurization apparatus. The contoured heart assist device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization. The pressurization apparatus is in communication with the one or more fluid connections of the contoured heart assist device and includes a pressurization mechanism and a depressurization mechanism. The pressurization apparatus can apply pressure to the contoured heart assist device and remove pressure from the contoured heart assist device. The pressurization apparatus is controllable to allow for different cycling rates between pressurized and depressurized states.

The present invention relates to a direct cardiac compression device, particularly a soft-shelled direct cardiac compression device, and methods of implanting it. In particular it relates to a soft-shelled direct cardiac compression device that proactively modulates the strain pattern in the heart during contraction so as to reduce apoptosis in the myocardium and/or induce beneficial growth and remodeling of the myocardium and/or scarred regions. In particular, the device of the present invention does not invert or grossly perturb the curvature of the heart during contraction.

In some embodiments of the invention, the strain pattern is a physiological strain pattern, near physiologic strain pattern or a strain pattern that is not aberrant. A physiological strain pattern, for the purposes of the present invention, is one which does not invert or grossly alter the heart's curvature during systole. The invention may also maintain a normal curvature or strain pattern during diastole, or relaxation of the heart.

Using some embodiments of the present invention in a patient, for example to eliminate dyskinesis in the borderzone, preserves myocardium and minimizes infarct expansion and secondary complications, e.g., cardiogenic shock, ventricular rupture and CHF.

Many devices of the present invention may be inserted through a small incision. Many devices may also be attached to the atrial appendages via clamps that may also be used to synchronize the device to the electrocardiogram (ECG) or to pace the heart relative to the device activation.

Abnormal Strain Pattern. Cardiac strain patterns appear to be a major controller of myocardial growth, remodeling, and recovery. The exact normal or physiologic strain pattern of the heart is not currently known. Tests to determine the normal strain pattern in the heart of eight healthy sheep using bi-plane x-ray data of radio-opaque markers produced eight distinctly different patterns. It appears that cardiac contraction is similar to gait; there are gross similarities amongst individuals (e.g., toe off and hip twist), but the details can be distinctly different (e.g., angle of leg at toe off, amount and timing of the hip twist). In fact, we can often recognize people from their gait. It is difficult to describe a normal gait, yet it is quite easy to classify abnormal gaits. Likewise, normal cardiac strain pattern is difficult to define and prescribe, yet it is quite easy to identify abnormal cardiac strain patterns (e.g., dyskinesis and hypokinesis).

Thus, although some embodiments of the present invention may be able to produce a normal cardiac strain pattern, the same or other embodiments may also be able to eliminate or reduce abnormal strain patterns.

Importance of Strain in Ventricular Recovery. Ventricular recovery is needed and is possible. Fortunately, many researchers are addressing ventricular recovery with different approaches (e.g., surgical, drug, and gene therapy, stem cells and/or tissue engineering; see FIG. 1). However, it is well established that mechanical stimuli (e.g., stress or strain) are important epigenetic factors in cardiovascular development, adaptation, and disease (Taber, 2001; Humphrey, 2002). In the vasculature, for example, it appears that perturbed loading conditions heighten the turnover of cells (proliferation and apoptosis) and matrix (synthesis and degradation) in altered configurations, thus resulting in altered geometries, properties, and biologic function (Humphrey and Rajagopal, 2003). Just as similar mechanisms appear to be operative in hypertension, aneurysms, and micro-gravity induced changes, it is likely that they are operative in cardiac disease (Omens, 1998).

CHF is compelling enough, yet dyskinesis or aberrant motion of the myocardium during contraction is likely important in all diseases of the heart that involve remodeling of the myocardium. Clearly, borderzone myocardium is viable (Bax et al., 2001) yet overloaded to the extent that it is dyskinetic, i.e., lengthens when it should shorten. It is likely that overloading leads to aberrant remodeling because (see review by Kherani et al., 2004) offloading leads to: normalization of genes that regulate calcium handling (Heerdt, et al., 2000), tumor necrosis factor (Torre-Amione et al., 1999) and cytoskeleton proteins (Wolff, et al., 1996); regression of fibrosis and cellular hypertrophy (Bruckner et al., 2001, Zafeiridis et al., 1998), and improved in-vitro contractile function (Dipla et al., 1998). Too much offloading is suspected to result in heart atrophy (Kherani, et al., 2004), whereby gradual weaning from a device should be sought along with combination therapy such as with clenbuterol (Hons et al., 2003).

Cellular and subcellular investigations have established that altered hemodynamic loading leads to growth and remodeling of myocytes and extra-cellular matrix (Grossman, 1980; Cooper, 1987; Weber et al., 1993; and Gerdes and Capasso, 1995) and myocytes are very sensitive to perturbations in strain and respond with altered gene expression (Komuro and Yazaki, 1993; Sadoshima and Izumo, 1997). Abnormal cardiac kinematics is often considered as a symptom of heart failure when in actuality it may be a primary cause of the aberrant growth and remodeling. By eliminating aberrant strain patterns with a device such as that of the present invention, it is possible that the growth and remodeling will stop being abnormal and start being restorative. Eliminating hypokinesis, for example, may reduce apoptosis, enhance myocyte development from native stem cells, and lead to ventricular recovery. Other CHF mechanisms or co-contributors are, among others, loss of myocyte shortening capability (Figueredo et al., 1994; Marian et al., 1997), calcium dysregulation (Feldman et al., 1993; Gwathmey et al., 1987), and unspecified myocyte apoptosis (Sabbah et al., 1998; Kajstura et al., 1995).

Artificial Hearts and Heart Assist Devices. There are numerous histories of artificial hearts and heart assist devices (Cooley and Frazier, 2000; Helman and Rose, 2000; Goldstein et al. 1998). FIG. 1 is a table that illustrates the various therapies that can be used. The various heart therapies 10 can be divided into electrical and pharmacological therapies 12 and mechanical therapies 14. The mechanical therapies 14 may be further divided into and include heart contracting therapies 16, which includes active devices 18. The active devices 18 include strain promoter devices 20. The mechanical therapies 14 commonly include blood contacting therapies 22, e.g., aortic balloon pump, axial flow, diaphragm and extracorporeal devices and therapies. The heart contracting therapies 16 commonly include surgical and passive devices 24, e.g., Left vectomy, cooley procedure, batista procedure, cardiomyoplasty, stem cell treatments and myosplint treatments. The active devices 18 include strain promoter devices 20 and ejection promoters and massagers 24. The ejection promoters and massagers 24 include parravicini treatment, anstadt treatment, hewson treatment, vineberg treatment, heart booster, cardiosupport system, DCC patch and so forth. The strain promoter device 20 includes the present invention. The various therapies in FIG. 1 (i.e., drugs, biventricular pacing, stem cell therapies, blood contacting assist devices, surgical manipulations, or passive stents and constraints etc.) typically off-load the heart and thus only modulate the strain pattern indirectly (e.g., through greater ejection fraction). Only direct cardiac compression devices (DCCDs) can directly induce a particular strain pattern. However, most prior DCCDs have been developed for enhancing ejection fraction or for ease of implantation rather than for strain modulation. Most induce aberrant strain patterns during contraction.

Cardiomyoplasty is a form of direct cardiac compression wherein a patient's own skeletal muscle is wrapped around the heart and stimulated during systole. Yet, the complications for cardiomyoplasty are significant: high peri-operative mortality and lengthy conditioning period (Oz et al., 2002). Similar to the recent special issue of Cardiology (2004, Volume 101, No. 1-3, Surgical Options for the Management of Congestive Heart Failure), cardiomyoplasty is considered in FIG. 1 as a surgical reconstruction as opposed to a method of cardiac assist.

Figure 9:
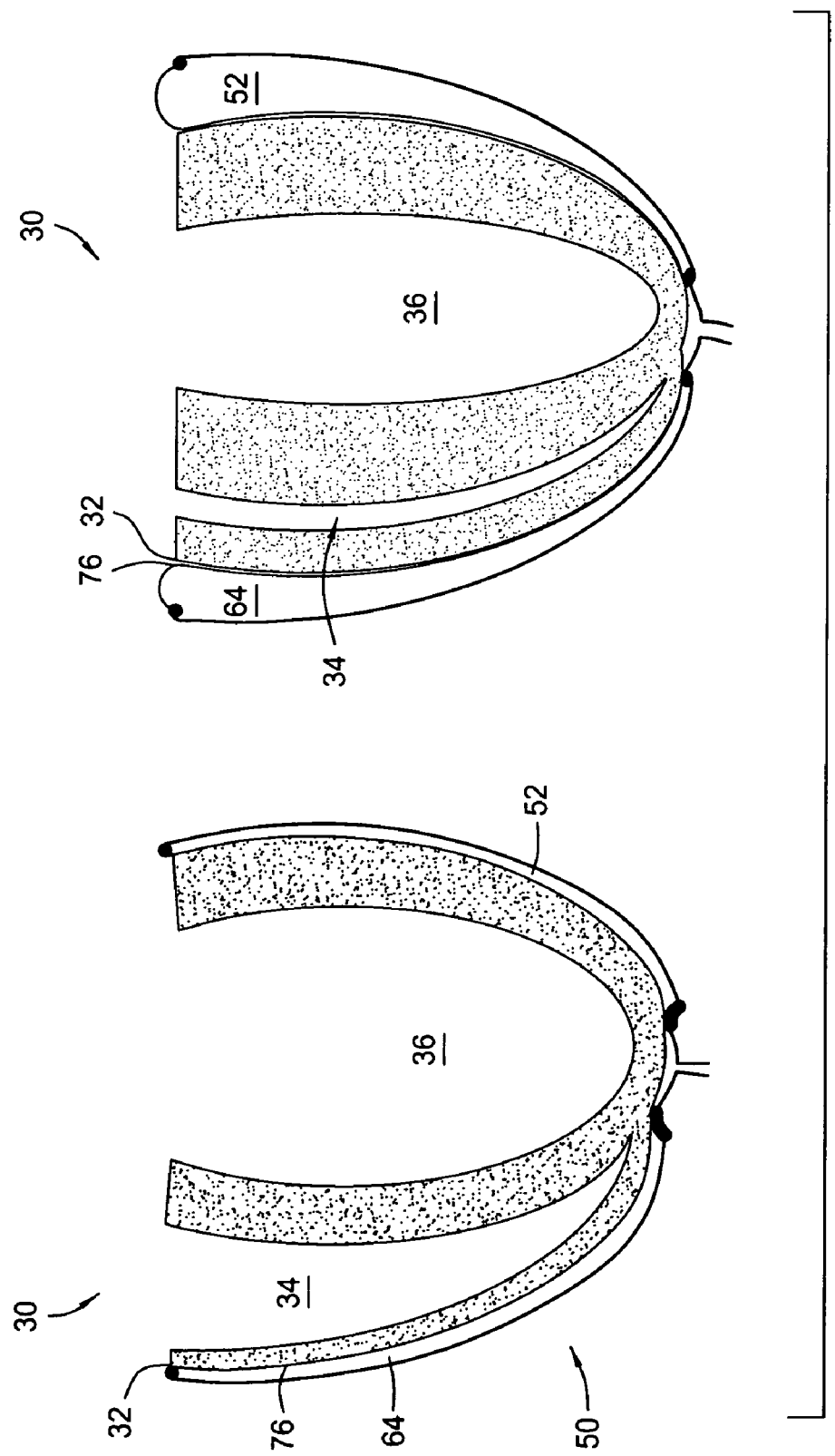

FIGS. 2A-2D shows the normal, null, and inverted curvature in apex-to-base, radial plane (long axis) of the heart. FIG. 2A illustrates a normal or positive curve with the inside of the curve toward the chamber, where the top references the base and the bottom references the apex. FIG. 2B illustrates a null curvature. FIG. 2C illustrates an inverted or negative curvature where the inside of the curve is away from the chamber. FIG. 2D is an illustration that shows the curvature inversion of the Anstadt cup as illustrated in FIG. 9 of the Anstadt patent (U.S. Pat. No. 5,119,804). DCCDs have been characterized as most promising with good hemodynamics and ease of implantation (Karvarana et al., 2001; Anstadt et al., 2002; Oz et al., 2002). A number of DCCDs are being developed. The Anstadt cup is shown in FIG. 2 (Anstadt et al., 2002). The CardioSupport System by Cardio Technologies Inc. (Pine Brook, N.J.) is similar to the Anstadt cup. The attachment is via vacuum on the apical end and the assist is via inflation of a membrane that lies between a rigid shell and the epicardial surfaces of the right ventricle (RV) and left ventricle (LV) (Williams and Artrip, 2001). The devices of Parravicini (1985) and the AbioBooster (Karvarana et al., 2001) by Abiomed Inc. (Danvers, Mass.) are sewn to the interventricular sulci, and elastic sacks between the shell and the epicardial surface are inflated during systole. The DCC Patch by Heart Assist Tech Pty Ltd (NSW, Australia) is similar to the Abio-Booster. It is described in a news release of the Australian Technology Showcase as " . . . two patches shaped to suit the profile of the heart . . . inflated and deflated in synchrony with the heart . . . ".

The heart booster (Kung et al., 1999) is composed of longitudinal tubes that have elliptical cross-sections with the major axis of the ellipse in the hoop direction. FIGS. 3A-3D shows the normal, increased, decreased, and inverted curvature in short axis sections of the heart as well as the inverted curvature produced by the existing Kung et al. device.

Figure 3A:
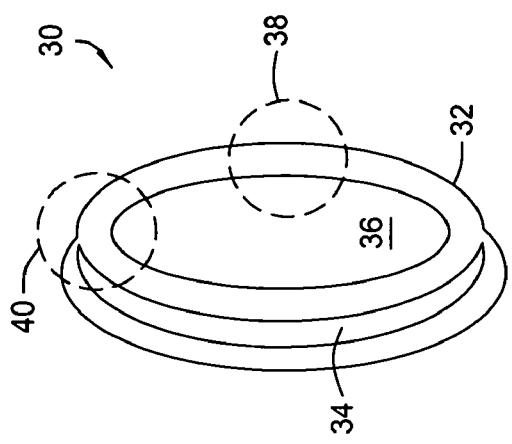
FIG. 3 is a schematic that illustrates the normal, increased, decreased and inverted curvature in short axis sections of the heart.
Figure 3B:
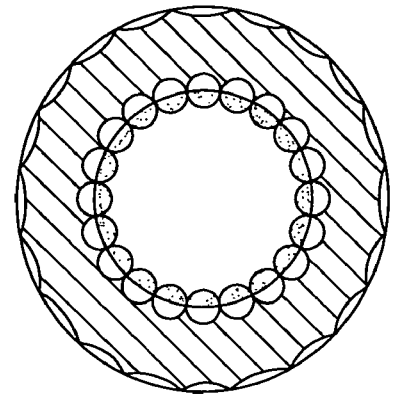
Figure 3C:
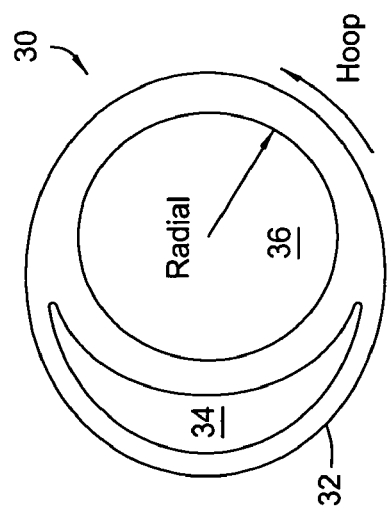
Figure 3D:
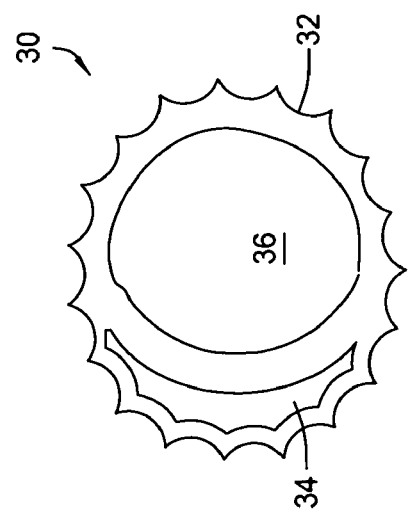

FIG. 3A illustrates the normal curvature of the heart 30 having an epicardium 32 and interior regions 34 and 36. The interior regions 34 and 36 have radii and curvatures that can be compared in different states. FIG. 3B illustrates the increased curvature of the heart 30 haying the epicardium 32 and interior regions 34 and 36. The interior regions 34 and 36 for a radii and curvature that is different than FIG. 3A. The interior regions 34 and 36 show a decreased curvature region 38 and an increased curvature region 40. FIG. 3C illustrates a heart 30 having the epicardium 32 and interior regions 34 and 36 with an inverted or negative curvature on the epicardial boundary. The inverted or negative curvature on the epicardial boundary is illustrated by the scalloped shape of the epicardium 32. FIG. 3D illustrates the pressurized tube cross-sections of the device disclosed in Kung, et al. Early DCCDs were designed for heart massage during open chest procedures. They were not designed to be implanted because implant science was just beginning and advances in biomaterials and infection management had not yet occurred. The Vineberg (1958) and Hewson (1962) devices have bladders that inflate rhythmically inside a rigid shell.

To understand how all of these DCCDs induce aberrant strain patterns, it is extremely important to note that contraction strain depends on both the end-diastolic configuration (reference configuration) and the end-systolic configuration (current configuration). The strain field is a function of the gradient (with respect to reference position) of the mapping of material points from the reference configuration to the current configuration. Thus, the fact that prior DCCDs fit the diastolic configuration is inconsequential to achieving an appropriate contraction strain pattern because their end-systolic configurations are grossly aberrant. Although strains induced by such motions as torsion may not perturb the heart geometry; if the overall geometry is abnormal, then the strain must be abnormal. Unphysiological geometries are illustrated in FIGS. 2 and 3.

Generally, the curvature is inversely proportional to radius-of-curvature and that curvature changes sign when the origin of the radius-of-curvature changes sides. As should be evident from FIG. 2D, curvature inversion can greatly increase ejection fraction. However, the curvature of the ventricles in a normal heart does not invert during systole, thus rendering such motions grossly abnormal. A healthy heart, moreover, will resist having its curvature inverted and Artrip et al. (1999) shows that heart function needs to decline by 30% before the effect of "non-uniform direct cardiac compression" becomes noticeable. In short, the heart resists assist when a DCCD induces aberrant strains. DCCD devices described above induce motions that are grossly abnormal. The Vineberg device inverts curvature in long axis planes and short axis planes. The Anstadt cup and Cardio-Support System invert curvature in long axis planes yet preserve curvature in the short axis planes. The AbioBooster, DCC Patch, Hewson device, and Parravicini devices pull on the interventricular sulci and push on the freewall such that the curvature will increase at the sulci and decrease on the freewalls (see FIG. 3B). The Heart Booster inverts curvature in short axis planes, yet preserves curvature in the long axis planes. Because they were not designed to eliminate aberrant motions, it should not be surprising that these existing DCCDs described above induce aberrant strain patterns.

Additionally, none of the existing DCCDs described above are implanted in a minimally invasive fashion, and such an implantation method is highly desirable, clinically useful, and commercially advantageous. Given that strain is a primary stimulus of myocardial growth and remodeling, there is a need for a DCCD that eliminates dyskinetic or hypokinetic motions in the heart.

Figure 4A:
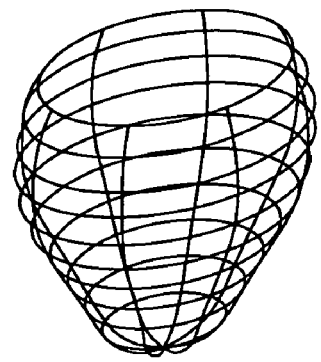
FIGS. 4A-4C arc images that illustrate one embodiment of the heart device with a bovine heart inside.
Figure 4B:
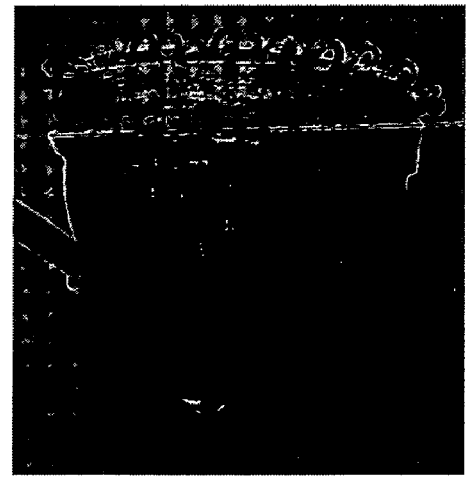
Figure 4C:
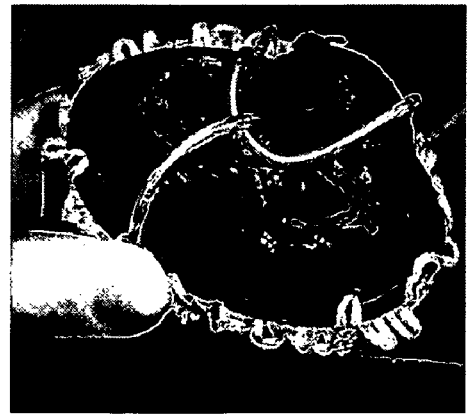

FIG. 4A shows a digital heart template determined from four ultrasound measurements. The template was used to produce the completed device seen in FIG. 4B and show in FIG. 4C attached to the heart of a young bovine. A prototype of a DCCD that proactively modulates the strain pattern during contraction has been constructed by Criscione et al. The prototype had a hard outer shell, and was implanted in a young bovine with pharmacologically induced heart failure (with esmolol hydrochloride, 7.5 mg/kg IV, as in Anstadt et al., 2002). Based on basic measurements (apex-base length, major and minor diameters, and distance from apex to equator) obtained from ultrasound, the device was constructed out of fiberglass, latex, brass, and nylon (FIG. 4). Because it was designed for acute experiments, there was no need for special manufacturing (i.e., removal of particulates and contaminates) or use of non-immunogenic materials (e.g., polyurethane and Ti).

This device, described in U.S. patent application Ser. No. 10/870,619, filed Jun. 17, 2004 (the '619 Application), which is incorporated by reference herein, is the first implantable device to proactively modulate the strain pattern during contraction. The class of devices claimed in the '619 Application are those that apply direct cardiac compression in a manner such that the end-diastolic and end-systolic configurations are physiologic with normal cardiac curvature, i.e. the class of direct cardiac compression device that achieve cardiac rekinesis therapy. The device disclosed in the '619 Application must be attached to the valve plane of the heart. An attachment developed in benchtop trials consists of suture runs along the right and left free walls together with stents that go from the device shell to the center of the valve plane via the transverse pericardial sinus (anterior stent) and oblique pericardial sinus (posterior stent). In addition to keeping the heart in the device, the stents eliminate the need to suture near the coronary arteries in the interventricular sulci. The highly elastic membrane on the epicardial surface is sealed tightly with the rigid shell to contain the pneumatic driving fluid (e.g., air). A typical membrane requires about 1 kPa (10 cm $H_2O$) of vacuum to unimpede heart filling. This is similar to that of the native heart which typically requires about 9 cm $H_2O$ of transmural pressure to fill (e.g., 6 cm $H_2$) of venous pressure minus a negative 3 cm $H_2O$ of intrathoracic pressure). The pressure waveforms (with compression for systole and tension for diastole) were generated by a Superpump System made by Vivitro Systems Inc. for cardiovascular research. The sync out signal was amplified, made bipolar, and used to pace the heart via right atrium (RA) leads.

One method of overcoming some negative effects of a hard-shelled DCCD (e.g., the need for a large thoracotomy) is to use a soft-shelled device. Soft-shelled devices include DCCDs with primary components that are constructed out of highly deformable materials. Such DCCDs can be collapsed and possibly implanted through a small incision this is likely to be sub-xiphoid (e.g., inferior to the xiphoid process) or a left thoracotomy. The Abiobooster and Heart Booster are currently existing shoft-shelled devices. However, as described above, both of these devices induce an aberrant strain pattern in the heart. Additionally, implantation methods for these devices still require sewing the devices to the heart or pericardium.

It is evident that mechanical stimuli (e.g. stretching) induce altered gene expression in myocytes, and recent evidence suggests that such stimuli guide growth and remodeling of myocytes and ECM. Yet at first glance, heart failure should not occur if the myocardium uses mechanics to guide its growth to better meet the mechanical loads. However, upon assuming that there is a physiologic dynamic range (PDR) in which the growth and remodeling processes perform appropriately, it becomes evident that heart failure could be a classic type of instability, i.e., a unidirectional unchecked progression. Indeed, the insidious nature of CHF alone suggests that CHF is unstable growth and remodeling.

Figure 5:
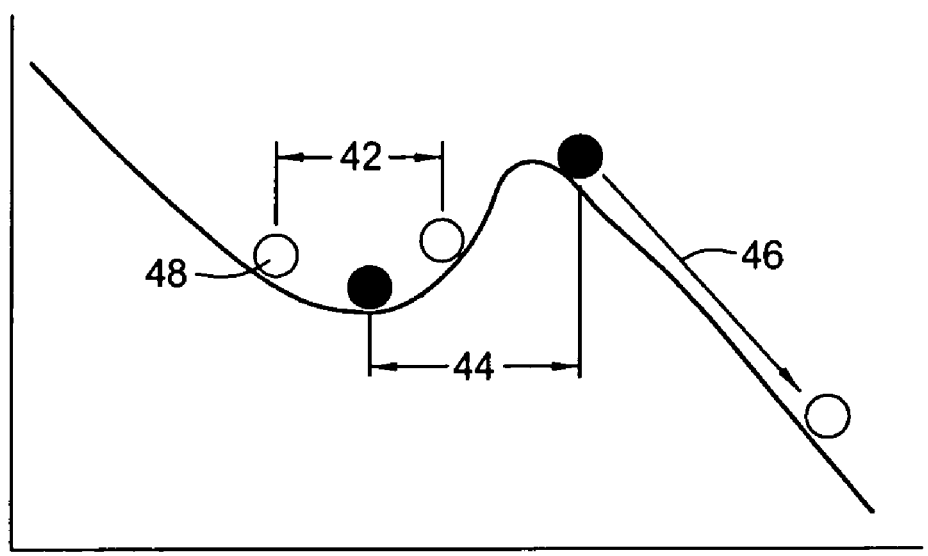
FIG. 5 is a graph that illustrates the growth stages in CHF.

FIG. 5 illustrates the "ball in a well" analogy for stability, instability and destabilizing events. The graph illustrates 3 regions the stable perturbations state 42, the destabilizing event 44 and the unidirectional unchecked progression 46. The PDR is the part of the curve that forms a well or the stable perturbations state 42 (i.e., where perturbations are met with restoration processes that bring the ball or heart back to an equilibrium or stable state). However, if there is a destabilizing event 44 such as a severe coronary stenosis that brings the heart (i.e., ball 48) outside of the stable perturbations state 42 or PDR, then a unidirectional, unchecked progression 46 or instability will ensue. For example, 68% of CHF cases are initiated by coronary artery disease, Gheorghaid and Bonow, 1998. Other stimuli, such as infection, over-pacing or atrial ventricular ("AV") shunting may also act as destabilizing events 44. This simplistic model for heart failure is supported by the fact that all these inducers or destabilizing events cause similar growth and remodeling (i.e., they result in a large, thin heart). Common statements such as "the heart is overloaded" suggests that the current state is unphysiologic or outside the stable perturbations state 42 or PDR. Moreover, treatments that "off-load the heart" are perhaps bringing the heart back into its PDR or stable perturbations state 42.

Although simplistic, such an instability paradigm is a model for heart failure. This model suggests that heart failure can be cured (via ventricular recovery) or prevented if the heart is off-loaded or returned to its PDR. Recent evidence supports such a mechanism for ventricular recovery. A recent modeling study (Guccione et al., 2001) suggests that wall stress is not an important inducer of the mechanical dysfunction in the borderzone of infarcts, thus it appears that strain or motion is the primary determinant. Hypokinetic or dyskinetic myocardium has aberrant motion despite possibly having a normal wall stress. The focus of preferred embodiments of the present invention is to push uniformly on the epicardial boundary during systole to restore the motion of the heart and eliminate hypokinesis and dyskinesis.

To model the treatment paradigm for embodiments of the present invention and grossly estimate what driving pressures are needed, one may use Laplace's law for a spherical vessel which gives an average wall stress ("σ") based on average radius ("R"), thickness ("H") and transmural pressure difference ($P_{in} - P_{out}$) where $P_{in}$ is the pressure in the ventricle and $P_{out}$ is the pressure outside the ventricle. In particular, $$\sigma = (P_{in} - P_{out})H/2R$$

Because blood is nearly incompressible, flow is dominated by pressure gradients (or less accurately by pressure differences). Without loss in generality, one may define blood pressure as its difference from atmospheric pressure. Because of ratification and densification, flows in compressible fluids are mediated by both pressure gradients and absolute pressure. Often $P_{out}$ is judiciously chosen as zero, yet for the present calculations, it is an important parameter because selected devices of the present invention are modulating $P_{out}$ by applying pressure to the epicardial surface of the heart.

The focus of some embodiments of the invention thus is to increase $P_{out}$ to obtain a lower σ and thus greater motion or ejection. For a large, thin, and hypokinetic heart, one may need to make σ at least as low as a normal heart.

Let $P_{in}$ be a typical mean systolic pressure (e.g., 7.5 kPa or approximately 100 mmHg). A typical thickness-to-radius ratio at end-diastole for a normal adult sheep is 1 to 2.5; whereas for overloaded, remodeled myocardium (as in the apical aneurysm model of Guccione et al., 2001) the thickness-to-radius ratio is about 1 to 4.

Using the equation above, to normalize σ with the same $P_{in}$, we would need a $P_{out}$ of 2.8 kPa. This is similar to the maximum driving pressure (approximately 3 kPa) used in in vitro tests described further in Example 2. For ventricular recovery, one will likely need external pressures that are about the same order as or slightly higher than pulmonary artery pressure. Hence, right ventricle ("RV") ejection fraction is expected to be nearly 100%. External pressure will be transferred through the incompressible RV myocardium and incompressible blood in the RV chamber, while RV outflow is accelerated. Kawaguchi et al. (1992) has demonstrated that uniform pressure applied to the entire epicardial surface will assist the heart at all levels of contractility.

Certain devices of the present invention can decrease RV input to compensate for the expected increase in RV output. Absent this capability it is likely that the RV and healthy regions of the LV would atrophy due to excessive off-loading. However, some devices of the present invention are ideal for weaning or gradually decreasing $P_{out}$, and the use of clenbuterol (Hons and Yacoub, 2003) has been shown to be useful in achieving ventricular recovery by preventing atrophy.

Devices and Implantation. To achieve a minimally invasive device of the class of the '619 Application devices, a soft-shelled DCCD has been constructed according to certain embodiments of the present invention. The device has inflatable, longitudinally oriented chambers that when deflated are collapsible. In addition, the deflated chambers are shaped and adjoined to form a structure that allows typical diastolic configurations. When pressurized the chambers push on the exterior of the heart in such a way as to induce a systolic configuration with normal curvatures.

Figure 6B:
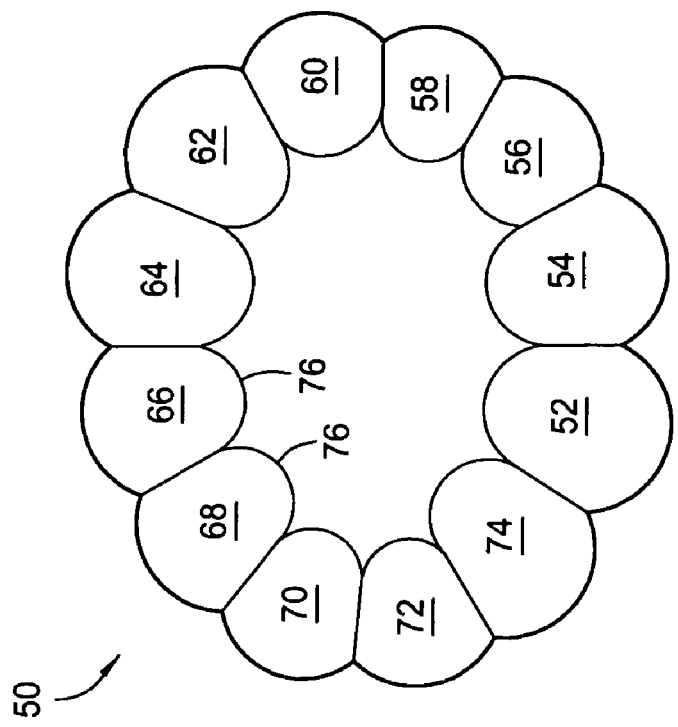
FIG. 6A is in the deflated state and FIG. 6B is in the pressurized state.
Figure 6A:
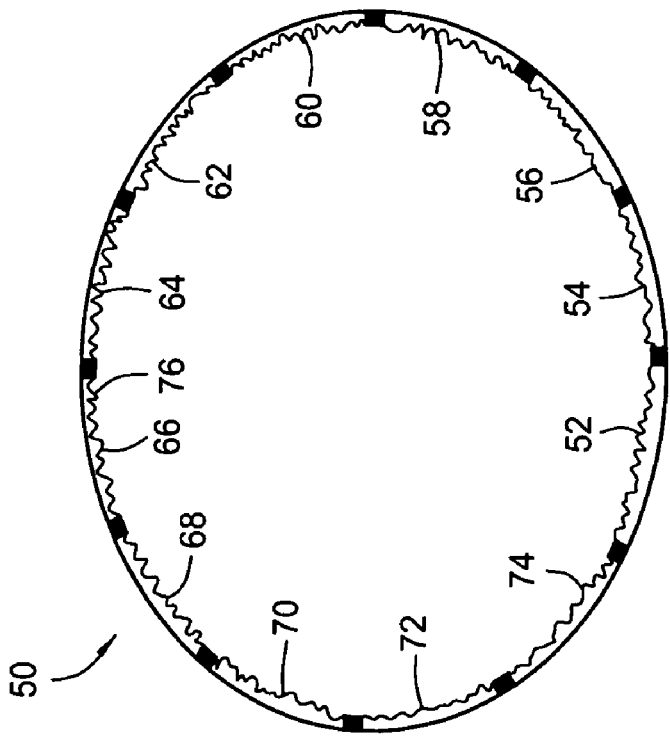

FIGS. 6A and 6B illustrate a horizontal cross section of one embodiment of the device 50 of the present invention in the deflated state FIG. 6A and the inflated state FIG. 6B. The device 50 includes 12 chambers 52-74 arranged with 4 chambers on the RV side and 8 chambers that are mostly on the LV but also overlapping the interventricular sulci. The chambers 52-74 are constructed from polyethylene film in one embodiment; however, other materials may be used. The side of the chambers 52-74 that are on the outer boundary form a shape that is similar to the end diastolic shape of the heart. The interior surface 76 has folds and crenulations such that when inflated the chambers 52-74 mostly expand inward.

Figure 7B:
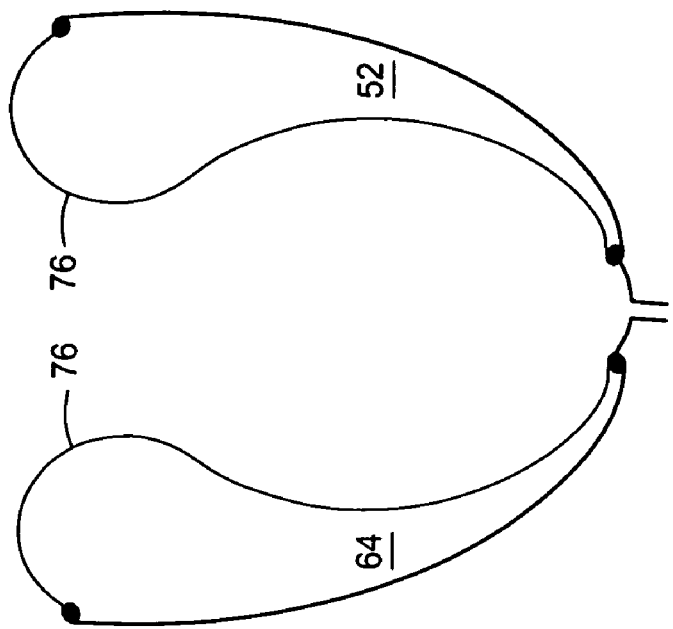
FIG. 7A is in the deflated state and FIG. 7B is in the pressurized state.
Figure 7A:
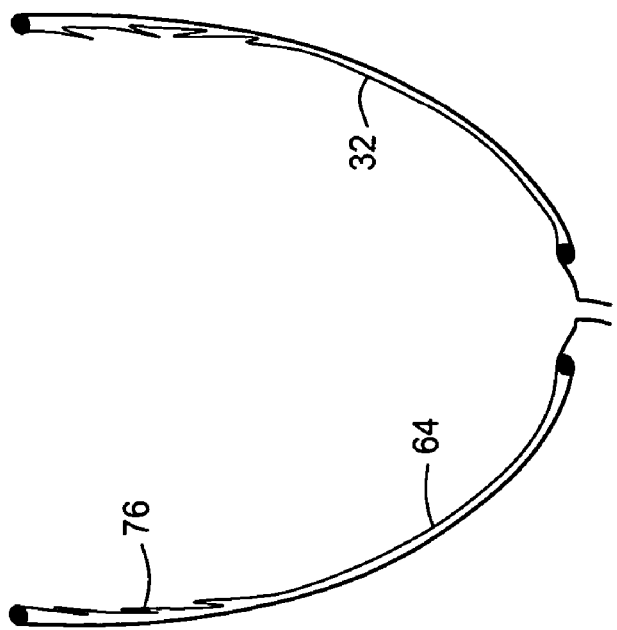

FIGS. 7A and 7B illustrate a vertical cross section of one embodiment of the device 50 of the present invention in the deflated state FIG. 7A and the inflated state FIG. 7B. Device 50 includes chambers 52 and 64 in the inflated and deflated states. The interior surface 76 of the chambers 52-74 that are on the outer boundary form a shape that is similar to the end diastolic shape of the heart. The interior surface 76 has folds and crenulations such that when inflated the chambers 52-74 mostly expand inward to contact the epicardium 32 of the heart 30.

FIGS. 8A and 8B illustrate a horizontal cross section of one embodiment of the device 50 of the present invention fitted to the heart 30. FIG. 8A is in the deflated state and FIG. 8B is in the inflated state. The device 50 includes 12 chambers 52-74 arranged with 4 chambers on the RV side and 8 chambers that are mostly on the LV but also overlapping the interventricular sulci. The chambers 52-74 include interior surface 76 that contacts the epicardium 32 of the heart 30. The side of the chambers 52-74 that are on the outer boundary form a shape that is similar to the end diastolic shape of the heart. The interior surface 76 has folds and crenulations such that when inflated the chambers 52-74 mostly expand inward. The shape of the interior regions 34 and 36 can be compared in the inflated state FIG. 8B and the deflated state FIG. 8A.

FIGS. 9A and 9B illustrate a vertical cross section of one embodiment of the device 50 fitted to the heart 30 in the deflated state FIG. 9A and the inflated state FIG. 9B. Device 50 includes chambers 52 and 64 in the inflated and deflated states. The interior surface 76 of the chambers 52-74 that are on the outer boundary form a shape that is similar to the end diastolic shape of the heart. The interior surface 76 has folds and crenulations such that when inflated the chambers 52-74 mostly expand inward to contact the epicardium 32 of the heart 30. The shape of the interior regions 34 and 36 can be compared in the inflated state FIG. 9B and the deflated state FIG. 9A.

Figure 8:
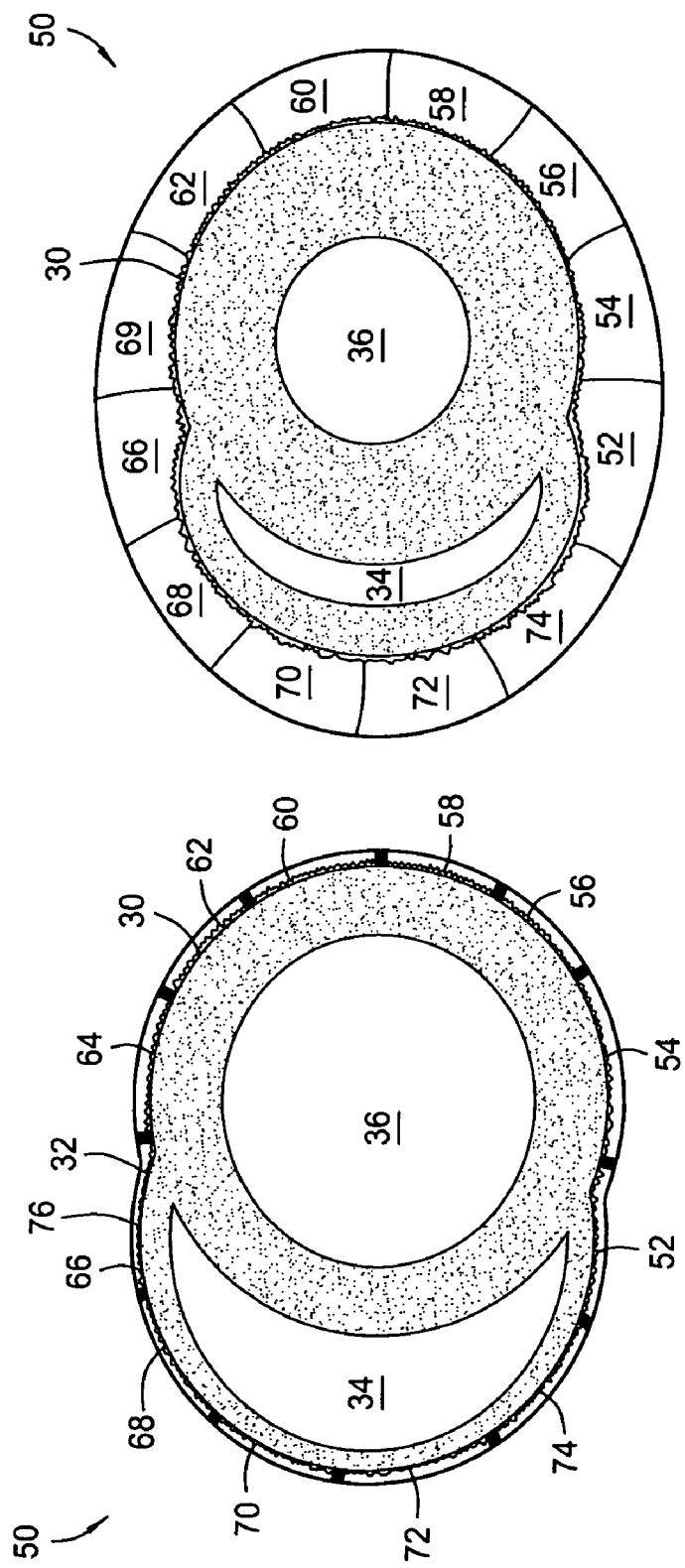

The fully pressurized shape without the heart inside is helpful for illustrating one device of the present invention, yet the shape will be significantly different when the device surrounds a heart which contains blood under pressure (see FIGS. 8 and 9). With a heart inside the pressure in the lumen of the device is higher than the pressure in the inflatable chambers. Because the chambers cannot fully expand, the inner film of the chambers is not taut. Rather than being supported by tension in the film (e.g., the right side of FIG. 6), pressure on the lumen side of the longitudinal chambers is supported by contact forces on the epicardial surface, e.g., the right side of FIG. 8. Without tension on the inner film, the attachment points are not drawn inward, e.g., the right side of FIG. 6. Instead, the shape of the outer sides of the chambers becomes circular to support the pressure within the chambers, e.g., the right side of FIG. 8. Note how the inner membrane is crenulated and thus not under tension. Consequently, the pressure in the device chambers applies direct pressure to the heart surface. In a similar manner, a blood pressure cuff applies direct pressure to the surface of a patient's arm.

Because the inflatable chambers taper (as they go from base to apex) in a manner that resembles natural cardiac curvature (see FIG. 7, right panel) the apex of the heart will have a physiological curvature. Moreover, because the device is rigid when pressurized, the curved shape of the apical end will act to prevent the heart from being expelled from the device. Basically, for the heart to leave the device the apical shape would have to pucker or a vacuum would need to form in the apical end of the device, both of which are unlikely.

Figure 10:
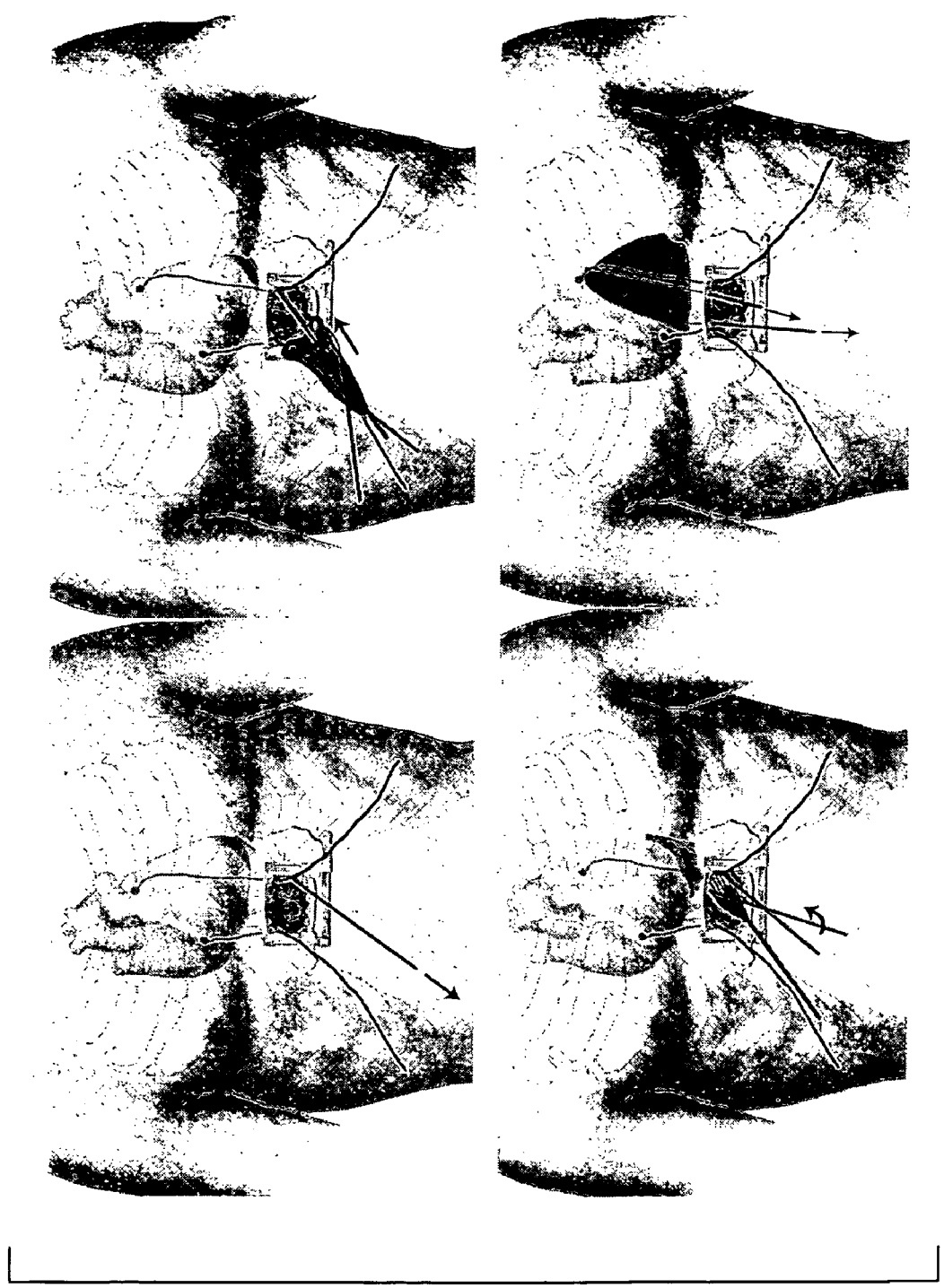
FIG. 10 shows a time series of the implantation method according to one embodiment of the present invention.

FIG. 10 diagrams one implantation method. Consequently, the device may be implanted with minimal attachment or sewing to the heart. Clamps on the atrial appendages are sufficient and useful for sensing the ECG or for pacing the heart. The access port on the apex (i.e., the hole in the bottom of the device) is useful for implantation and for removing fluid that could accumulate between the heart and device. Additionally, a biocompatible lubricant, anti-clotting, anti-fibrosis, or antibiotic agent may be injected into the space between the heart and device. So that the device may be removed easily after weaning, the device may be covered with a film that retards fibrous adhesions such as Surgiwrap®.

As noted above, because the RV operates at a lower pressure and has a thin wall, certain DCCDs of the present invention will enhance RV ejection more than LV ejection. As observed in the implantation of a prototype, driving pressures that are equal to or greater than pulmonary artery pressure may occur, resulting in a 100% RV ejection fraction is expected. Pulmonary congestion may result if RV output is continuously increased relative to LV output. Autoregulatory mechanisms may mitigate this enhancement of RV ejection over LV ejection. If not, separation of RV and LV chambers in the DCCD may be useful. In particular, it may be possible to impede RV filling with residual pressurization of the 4 RV chambers during diastole. By controlling input to the RV we may modulate the ratio of RV output to LV output. Pulmonary congestion was not seen in the implantation of at least one prototype of a hard shelled device, but this may have been due to tricuspid regurgitation rather than to autoregulatory mechanisms adjusting to the increase in RV ejection fraction. Because of the regurgitation, forward flow was not enhanced.

Figure 11:
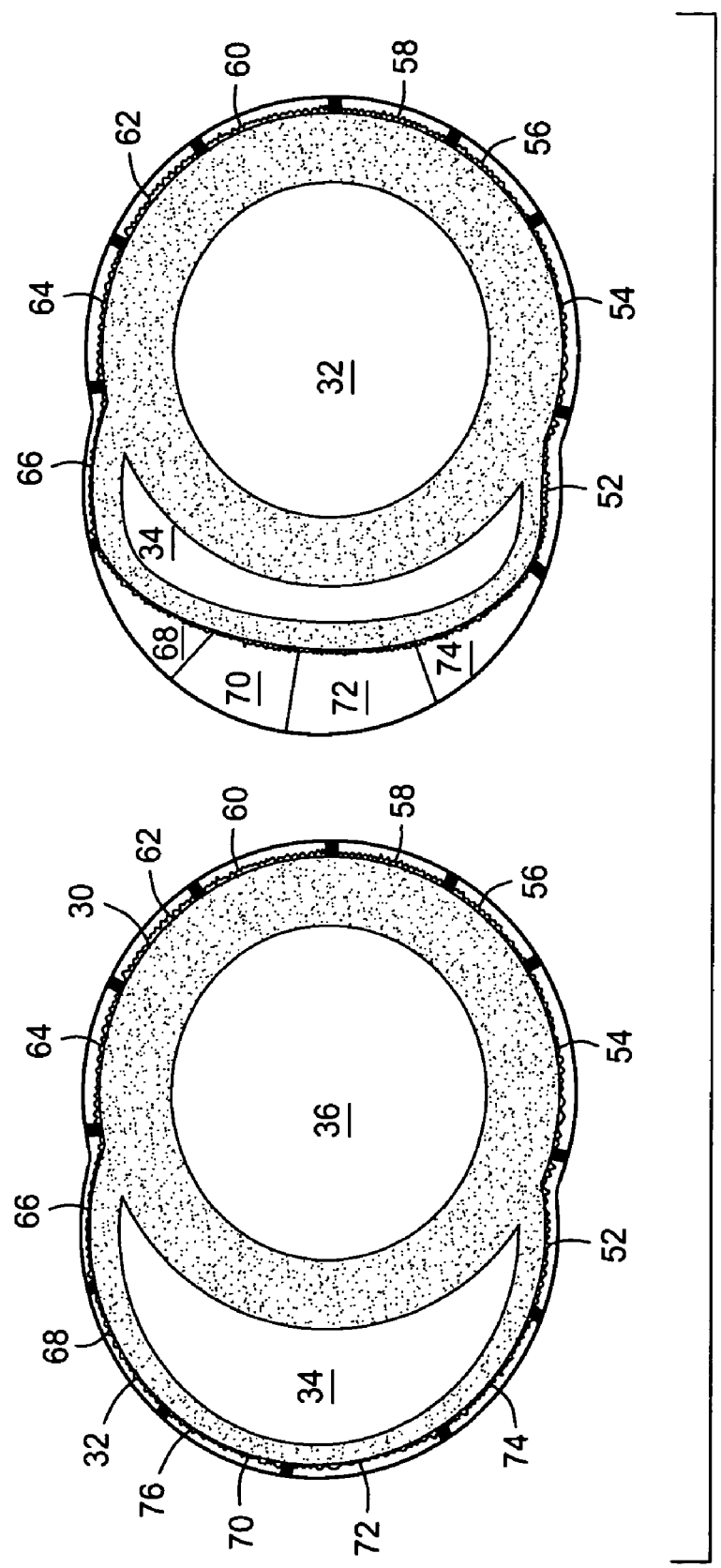
FIG. 11 is a schematic diagram of one embodiment of the present invention configured to reduce right ventricle input by reducing right ventricle filling.

FIG. 11 illustrates how RV input (i.e., filling) can be modulated by the application of residual RV epicardial pressure (RRVEP). During diastole the myocardium is relaxed and the heart shape is easy to perturb. This is particularly true of the RV freewall because it is very thin. Hence, residual gas in the four chambers abutting the RV freewall will likely prevent the RV from filling while leaving the LV unperturbed. It is, in essence, easier to differentially modulate filling than to modulate ejection.

FIGS. 11A and 11B illustrate a horizontal cross section of one embodiment of the device 50 of the present invention fitted to the heart 30. FIG. 11A is in the deflated state and FIG. 11B is in the inflated state. The device 50 includes 12 chambers 52-74 arranged with 4 chambers on the RV side and 8 chambers that are mostly on the LV but also overlapping the interventricular sulci. The chambers 52-74 include interior surface 76 that contacts the epicardium 32 of the heart 30. The side of the chambers 52-74 that are on the outer boundary form a shape that is similar to the end diastolic shape of the heart. The interior surface 76 has folds and crenulations such that when inflated the chambers 52-74 mostly expand inward. The shape of the interior regions 34 and 36 can be compared in the inflated state FIG. 11B and the deflated state FIG. 11A.

A potential drawback is that the RV freewall may atrophy because RV volume will be chronically decreased and native RV stroke work will be decreased. Fortunately, a device that proactively modulates the strain pattern is ideal for weaning the heart from a device because assist can be graded. Most previous DCCDs only assist when the heart is weak enough to be grossly deformed.

The following examples are provided to further explain specific examples of the invention. They are not intended to represent all aspect of the invention in its entirety. Variations will be apparent to one skilled in the art.

Example 1

Direct Cardiac Compression Device

Figure 12:
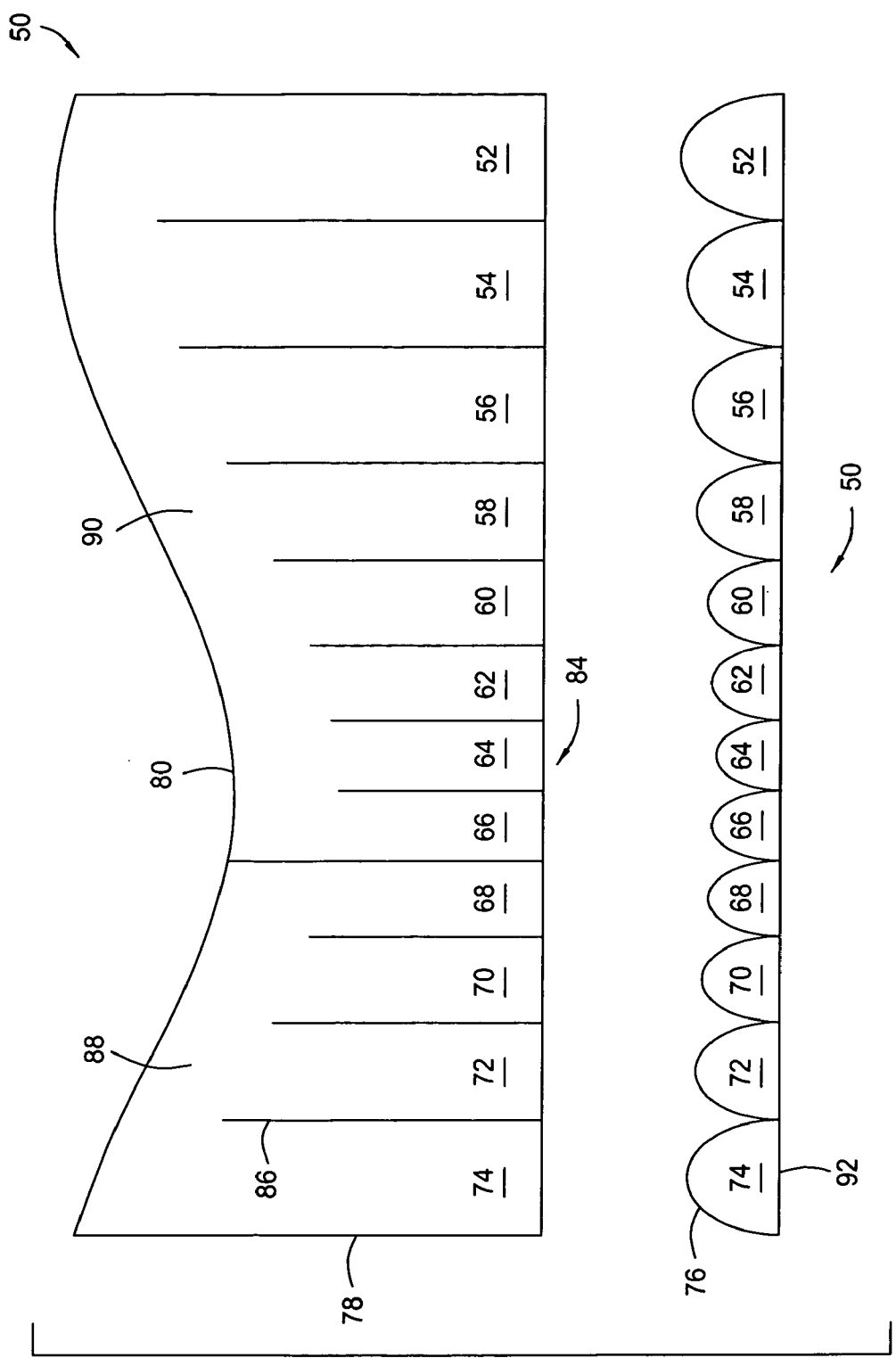
FIG. 12 is a schematic diagram illustrating the layout of a first series of heat welds between two polyethylene sheets.

FIGS. 12A and 12B are front view and horizontal cross sectional view of the present invention respectively. FIG. 12A illustrates the device 50 having a surface 78 having a basal edge 80 and an apical edge 84. The surface 78 includes welds 86 to form the chambers 52-74 and include the 4 right ventricle chambers 88 and the 8 left ventricle chambers 90. FIG. 12B illustrates the device 50 having an interior surface 76 on the endocardial side and an exterior surface 92 on the pericardial side. Welds 86 are used to form the chambers 52-74. In some embodiments, the interior surface 76 is made of 2 mils thick polyethylene and the exterior surface 92 is made of 6 mils thick polyethylene; however the skilled artisan will recognize other thickness (e.g., 0.1 to 12 mils) and other materials may be used.

Figure 13:
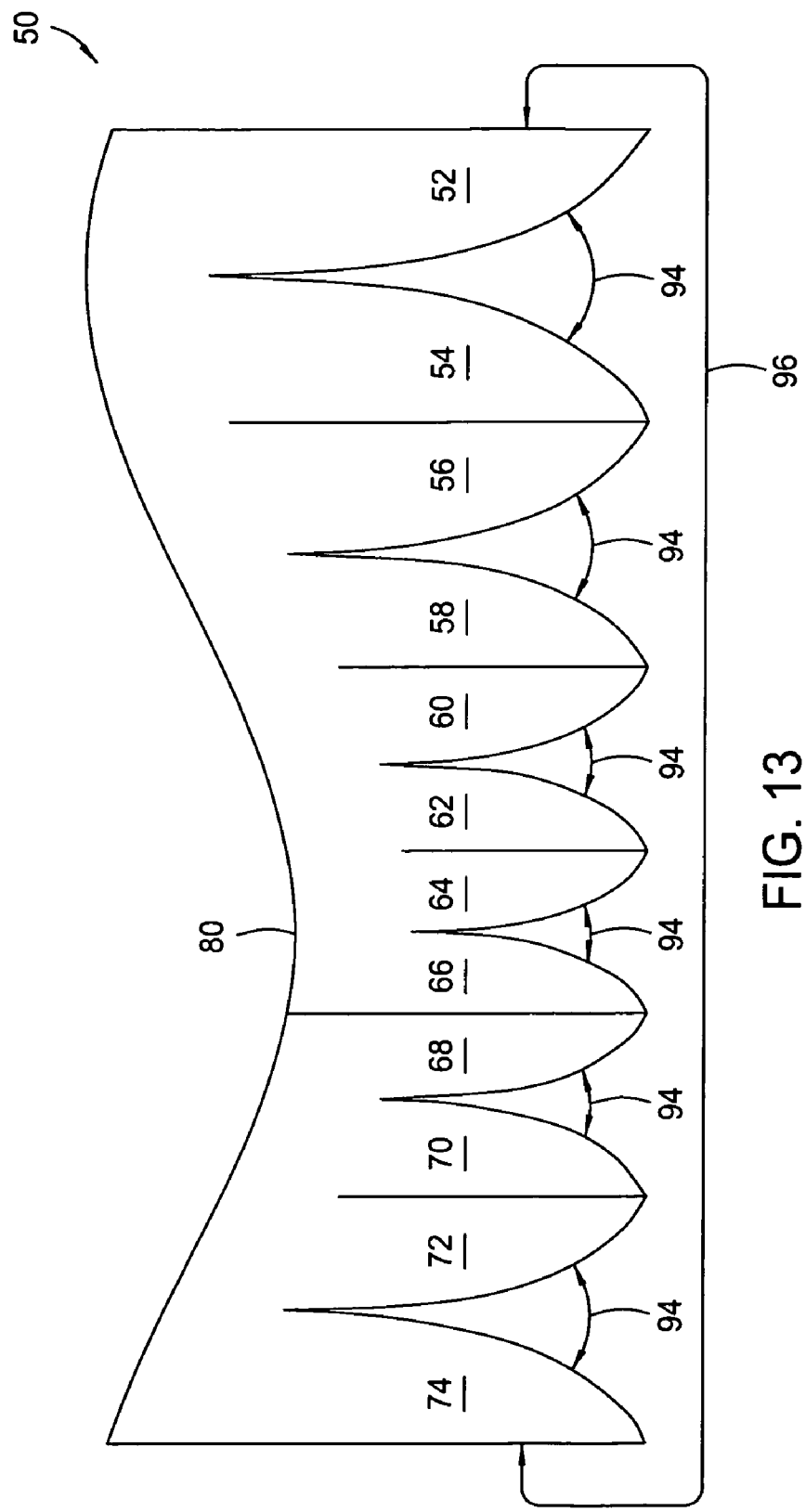
FIG. 13 is a schematic diagram illustrating the layout of the second and third series of heat welds to produce a device according to an embodiment of the present invention.

By heat welding two polyethylene sheets together along particular folds (as see in FIGS. 12 and 13), a prototype DCCD according to an embodiment of the invention was constructed (see FIG. 14). FIG. 13 illustrates the device 50 having a surface 78 having a basal edge 80 at the basal end of posterior interventricular sulcus. A second weld 94 is used to secure the chambers 52-74 and the device 50 is completed by a third weld 96 to the device in FIG. 14.

Except for the crenulations, the first two series of welds were done with the sheets lying flat. Upon completing the third series of welds, the device took on its 3D final shape. To make the heat welds, brass rods (for the straight welds) and bent copper plates (for the curved welds) were heated in an oven at about 180° C. for about 1 hour and then held against the sheets at the proper position for about 40; seconds. A non-stick polymer (e.g., Hama Inc) was placed between the bars and the polyethylene sheets. The polymer was designed for household crafts, which involve melting plastics with a clothes iron. The pneumatic drive lines (see FIG. 14, but not shown in FIGS. 12 and 13) were inserted through grommets fastened to the device with gaskets to seal the attachment and avoid stress risers. Additionally, there is an apical hole in the device, which was made by blunting the apical tips of the 12 chambers. To be more specific, the hole is not in the chambers, but the chambers do not come together at the apical end, thus leaving a hole. Through this hole one may remove fluid or air that accumulates between the device and the heart.

A custom Matlab® program was written to calculate the weld layouts from the following three cardiac measurements that could be obtained from a cardiac ultrasound (at end-diastole): 1) distance from apex to base along the posterior epicardial boundary, 2) distance from apex to base along the anterior epicardial boundary, and 3) perimeter of the epicardial boundary from a short axis slice parallel to the valve plane at the level of the papillary tips. The output for an adult ovine heart obtained from the slaughterhouse was calculated. From the output the weld lines were transferred to the outer (uncrenulated) sheet. FIG. 14 shows the completed device with the ovine heart inside it and layout markings on the outer sheet.

In addition, the device of the present invention may contain multiple chambers each independently controllable to allow customizing of the device for a particular condition. For example, one embodiment includes 12 chambers with 2 chambers that allow the pressure of the chambers to be regulated independently.

Example 2

In Vitro Testing

The device of Example 1 was tested on the benchtop and loaded with about 9 kPa of pressure. Based on previous experiments with an earlier device, it was expected to use driving pressures below 5 kPa. An important finding from this benchtop test was that the heart was not ejected from the device when the device was pressurized. This is an important design feature because sewing to the heart will not be needed and interference with the heart valves will be minimal. There were small leaks in the device, but leak proof devices are not required for most uses. Instead, one may place drains to vacuum on the apical end: one in the apical hole to remove air and fluid between the device and heart, and one to remove air and fluid between the device and mediastinum. Lost pneumatic driving fluid may be replaced as necessary.

This embodiment has also been tested in a live sheep, as expected from the benchtop trials, the device could be easily slipped over the heart utilizing a sub-xiphoid incision. Moreover, without any attachments (i.e., sewing, clamping, or the like) the heart remained within the device (i.e., it was not ejected) during pressurization of the device.

The present invention provides a direct cardiac compression device (DCCD) that applies forces to the exterior, epicardial boundary of the heart. The device of the present invention has a shape with curvatures that are similar to the end-diastolic shape of the heart at the end-diastole of the cardiac cycle. In addition, it may be enabled to purposely restrict inflow to the right side of the heart, e.g., rightsided inflow restriction ("RSIR"). When it is enabled for RSIR, the device protrudes inward towards the right ventricle during diastole to decrease the end-diastolic volume of the right ventricle. Regardless, the present invention enables (or induces) the left ventricle to assume a shape with curvatures that are similar to the proper end-diastolic shape of the heart.

At end-systole of the cardiac cycle, the present invention has a shape with curvatures that are similar to the proper end-systolic shape of the heart. The present invention is active in the sense that energy is consumed to accomplish the shape change during systole and energy is liberated to accomplish the shape change during diastole. The energy source is from a pneumatic pressure source. During systole (i.e., shape change from end-diastole to end-systole) the device is inflated with a positive pressure. During diastole (i.e., shape change from end-systole to end-diastole) the device is deflated via suction. If enabled for RSIR, the device is not fully deflated during diastole because some residual pressure is applied to chambers that abut the right ventricle.

The present invention is soft or collapsible when deflated. In addition the present invention minimizes the risks of thrombosis and infection as there is no contact with the blood. Many of the devices in the art when pressurized are grossly abnormally shaped, evidenced by the various schemes used to attach the DCCD to the heart (e.g., sewing to ventricle, basal drawstring, apical suction cup, etc).

There is no need to attach the present invention to the heart because the heart is naturally drawn into the pressurized or activated device. Specifically, for the heart to leave the device (i.e., be extruded from the DCCD), the device curvature would need to invert, yet the device rigidity (when pressurized) resists curvature inversion. This is very useful because implantation time and complications due to attachment are minimized, i.e., when the activated shape of the device cavity (i.e., the inner wall of the DCCD which touches the epicardial or outer boundary of the heart) is nearly end-systolic shape. It can eliminate dyskinesis (defined as abnormal cardiac motions). Current evidence indicates that growth and remodeling in the heart are guided by mechanical stimuli such as the motion during cardiac contraction whereby the elimination of dyskinesis is of paramount importance. The device provides some of the pumping power demanded of the heart to energize or pressurize the circulatory system. Abnormal hearts often need to be "off-loaded" or be assisted with satisfying the circulatory demands of the body. In contrast, passive devices like Corcap or the Myosplint cannot provide power for pumping blood.

The device can be implanted in a minimally invasive manner through, for example, a small sub-xiphoid incision. Also, it enables a failsafe mechanism. In particular, the device does not hinder cardiac performance when the device is deflated or deactivated. In the embodiments herein, we completely deflate the device (default to vacuum) to make it soft and collapsible.

FIGS. 15A-15D are images that illustrate another embodiment of the present invention that includes one pressure chamber with eight interior supports in a fan-like arrangement. FIGS. 15A and 15B are images of the device without the outer covering attached, while FIGS. 15C and 15D are images of the device with the outer covering attached.

The purpose of the interior (inside the chamber as opposed to inside the cavity formed by the inner boundary of the DCCD) supports is to make the pressurized shape like the end-systolic shape of the heart. In similar fashion, the interior supports of an air mattress make the pressurized shape that of a mattress as opposed to that of spheroid. This prototype is made of latex, yet a device for implantation would be made of a flexible biocompatible polymer such as polyurethane. Being made of a highly flexible material, it is collapsible. The apical hole in the device is a useful feature that aids with implantation, e.g., by being able to draw the heart apex into the device via a suction cup threaded through the apical hole in the device. The apical hole is also useful for removing any fluid or air that leaks out of the device that would accumulate between the heart and device.

Figure 16:
FIG. 16 is an image that illustrates a device according to another embodiment of the present invention.

FIGS. 16A-16B are images that illustrate yet another embodiment of the present invention that includes supports interior to the chamber, however, it has a support interior to the cavity. Similar to the embodiment depicted in FIG. 15, this embodiment is a one chamber device; however rather than have supports interior to the chamber there are supports interior to the cavity. In particular, there are wires weaved to form a shape appropriate for the heart. When pushed on by the expanding chamber during systolic pressurization the wire weave allows the cavity to shrink, yet they force the cavity to have a curvature that is normal for end-systole. Wires made of super elastic metals like Nitinol allow the device to be soft or compressible for insertion. Other metals that may be used include shape-memory alloys like copper-zinc-aluminum, iron-manganese-silicon, gold-cadmium, copper-aluminum, copper-aluminum-nickel, and nickel-titanium.

Figure 17:
FIG. 17 is an image that illustrates a device according to yet another embodiment of the present invention.

FIGS. 17A-17B are images that illustrate still another embodiment of the present invention that includes supports interior to the chamber, however, it has a support interior to the cavity. Rather than wires made of super elastic metals that allow the device to be soft or compressible for insertion, this embodiment has six separate chambers, and the chamber dividers act as supports. When pushed on by the expanding chamber during systolic pressurization the cavity can shrink, yet they force the cavity to have a curvature that is normal for end-systole. This embodiment has been tested in 4 sheep and it was implantable in a minimally invasive fashion, failsafe, and able to eliminate dyskinesis caused by a myocardial infarction (heart attack). Also, by inflating the two chambers that abut the right ventricle, the central venous pressure was caused to rise by restricting the filling.

Generally when a material is implanted in the body, the body recognizes the presence of the foreign material and triggers an immune defense system to eject and destroy the foreign material. This results in edema, inflammation of the surrounding tissue and biodegradation of the implanted material. As a result the biomedical implantable material must be carefully selected. Examples of suitable, biocompatible, biostable, implantable materials include but are not limited to polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes and combinations thereof In addition, the present invention may be reinforced with filaments, made of a biocompatible, biostable, implantable polyamide, polyimide, polyester, polypropylene, polyurethane etc.

The incidence of infection associated with medical device implantation is often life threatening, e.g., entercoccus, pseudomonas auerignosa, staphylococcus and staphylococcus epidermis infections. The present invention may include bioactive layers or coatings to prevent or reduce infections. For example, bioactive agents may be implanted, coated or disseminated from present invention and include antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof. Antimicrobial agents include but are not limited to benzalkoniumchloride, chlorhexidine dihydrochloride, dodecarbonium chloride and silver sufadiazine. Generally, the amount of antimicrobial agent required depends upon the agent; however, concentrations may ranges from 0.0001% to 5.0%.

In addition, some embodiments of the present invention may have leads, electrode or electrical connections incorporated into the device. When present they may be made from noble metals (e.g., gold, platinum, rhodium and their alloys) or stainless steel. In addition, ordinary pacemaker leads and defibrillation leads could be also incorporated into the present invention to provide cardiac pacing or defibrillation.

Although the present invention and its advantages have been described in detail, it should be understood that various changes, substitutions and alterations can be made herein without departing from the spirit and scope of the invention as defined by the following claims.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

American Heart Association (2003). *Heart Disease and Stroke Statistics*—2004 Update. Dallas, Tex.: American Heart Association.

Anstadt, M. P., Schulte-Eistrup, S. A., Motomura, T., Soltero, E. R., Takano, T., Mikati, I. A., Nonaka, K., Joglar, F., Nose, Y. (2002). Non-blood contacting biventricular support for severe heart failure. *Ann Thorac Surg* 73: 556-62.

Artrip, J. H., Yi, G. H., Levin, H. R., Burkhoff, D., Wang, J. (1999). Physiological and hemodynamic evaluation of nonuniform direct cardiac compression. *Circulation* 100 (suppl II): 236-43.

Bax, J. J., Poldermans, D., Allhendy, A., Boersma, E., Rahimtoola, S. H. (2001) Sensitivity, specificity, and predictive accuracy of various noninvasive techniques for detecting hibernating myocardium. *Curr Probl Cardiol* 26: 141-186.

Bruckner, B. A., Stetson, S. J., Perez-Verdia, A., Youker, K. A., Radovancevic, B., Koerner, M. M., Entman, M. L., Frazier, O. H., Noon, G. P., Torre-Amione, G. (2001) Regression of fibrosis and hypertrophy in failing myocardium following mechanical circulatory support. *J Heart Lung Transplant* 20: 457-464.

Cooley, D. A., and Frazier, O. H. (2000). The past 50 years of cardiovascular surgery. *Circulation* 102: IV88-93.

Cooper, G. (1987). Cardiocyte adaptation to chronically altered load. *Annu. Rev. Physiol.* 49: 501-518.

Dipla, K., Mattiello, J. A., Jeevanandam, V., Houser, S. R., Margulies, K. B. (1998) Myocyte recovery after mechanical circulatory support in humans with end-stage heart failure. *Circulation* 97: 2316-2322.

Feldman, A. M., Weinberg, E. O., Ray, P. E., and Lorell, B. H. (1993). Selective changes in cardiac gene expression during compensated hypertrophy and the transition to cardiac decompensation in rats with chronic aortic banding. *Circ. Res.* 73: 184-192.

Figueredo, V., and Camacho, S. (1994). Basic mechanisms of myocardial dysfunction: Cellular pathophysiology of heart failure. *Curr. Op. Cardiol.* 9: 272-279.

Gerdes, A. M., and Capasso, J. M., (1995). Structural remodeling and mechanical dysfunction of cardiac myocytes in heart failure. *J. Mol. Cell. Cardiol.* 27: 849-856.

Gheorghiad, M., and Bonow, R. O., (1998). Chronic heart failure in the united states: a manifestation of coronary artery disease. *Circulation* 97:282-9.

Goldstein, D. J., Oz, M. C., Rose, E. A. (1998) Medical progress: implantable left ventricular assist devices. *N Engl J Med* 339(21): 1522-1533.

Grossman, W. (1980). Cardiac hypertrophy: Useful adaptation or pathologic process? *Am. J. Med.* 69: 576-583.

Guccione, J. M., Moonly, S. M., Moustakidis, P., Costa, K. D., Moulton, M. J., Ratcliffe, M. B., Pasque, M. K., (2001). Mechanism underlying mechanical dysfunction in the boarder zone of left ventricular aneurysm: a finite element model study. *Ann. Thorac. Surg.* 71:654-62.

Gwathmey, J. K., Copelas, L., MacKinnon, R., Schoen, F. J., Feldman, M. D., Gorssman, W., and Morgan, J. P. (1987). Abnormal intracellular calcium handling in myocardium from patients with end-stage heart failure. *Circ. Res.* 61: 70-76.

Heerdt, P. M., Holmes, J. W., Cai, B., Barbone, A., Madigan, J. D., Reiken, S., Lee, D. L., Oz, M. C., Marks, A. R., Burkhoff, D. (2000) Classic unloading by left ventricular assist device reverses contractile dysfunction and alters gene expression in end-stage heart failure. *Circulation* 102: 2713-2719.

Helman, D. N., Rose, E. A. (2000) History of mechanical circulatory support. *Progress in Cardiovascular Diseases* 43(1): 1-4.

Hewson, C. E. (1962), Inflatable heart massager. U.S. Pat. No. 3,034,501.

Hons, J. K. F. and Yacoub, M. H. (2003), Bridge to recovery with the use of left ventricular assist device and clenbuterol. *Ann. Thorac. Surg.* 75:S36-41.

Hosenpud, J. D., Bennett, L. E., Keck, B. M., Boucek, M. M., Novick, R. J., (2000). The registry of the international society for heart and lung transplantation: seventeenth official report. *J Heart Lung Transplant* 19: 909-31.

Humphrey, J. D., (2002). *Cardiovascular Solid Mechanics: Cells, Tissues, and Organs*. New York: Springer. p. 166-178, 674.

Humphrey J D, Rajagopal K R (2003) A constrained mixture model of arterial adaptations to a sustained step change in blood flows. *Biomech. Model Mechanobiol.* 2:107-126.

Kajstura, J., Zhang, X., Liu, Y., Szoke, E., Cheng, W., Olivetti, G., Hintze, T., and Anversa, P. (1995). The cellular basis of pacing-induced dilated cardiomyopathy. Myocyte cell loss and myoyte cellular reactive hypertrophy. *Circulation* 92: 2306-2317.

Karvarana, M. N., Helman, D. N., Williams, M. R., Barbone, A., Sanchez, J. A., Rose, E. A., Oz, M. C., Milbocker, M., Kung, R. T. V., (2001). Circulatory support with a direct cardiac compression device: a less invasive approach with the AbioBooster device. *J Thorac Cardiovasc Surg* 122: 786-787.

Kawaguchi, O., Goto, Y., Futaki, S., Ohgoshi, Y., Yaku, H., Suga, H. (1992). Mechanical enhancement of myocardial oxygen saving by synchronized dynamic left ventricular compression. *J Thorac Cardiovasc Surg* 103:573-81.

Kherani. A. R., Maybaum, S., Oz, M. C. (2004) Ventricular assist devices as a bridge to transplant or recovery. *Cardiol* 101:93-103.

Komuro, I., and Yazaki, Y. (1993). Control of cardiac gene expression by mechanical stress. *Ann. Rev. Physiol.* 55: 55-75.

Kung and Rosenberg (1999). Heart booster: a pericardial support device. *Annals of Thoracic Surgery* 68:764-7.

Marian, A., Zhao, G., Seta, Y., Roberts, R., and Yu, Q. (1997). Expression of a mutant (Arg92Gln) human cardiac troponin T, known to cause hypertrophic cardiomyopathy, impairs adult cardiac myocyte contractility. *Circ. Res.* 81: 76-85.

Omens, J. H. (1998). Stress and strain as regulators of myocardial growth. *Prog. Biophys. Molec. Biol.* 69: 559-572.

Oz, M. C., Artrip, J. H., Burkhoff, D., (2002). Direct cardiac compression devices. *J Heart Lung Transplant* 21: 1049-1055.

Packer, M., Coats, A J., Fowler, M B., Katus, H A., Krum, H., Mohacsi, P., Rouleau, J L., Tendera, M., Castaigne, A., Roecker, E B., Schultz, M K., DeMets, D L. Carvedilol Prospective Randomized Cumulative Survival Study Group. (2001). Effect of carvedilol on survival in severe chronic heart failure. *N Engl J Med* 344(22): 1651-8.

Parravicini (1985). U.S. Pat. No. 4,536,893.

Rose, E. A., Gelijns, A. C., Moskowitz, A. J., Heitjan, D. F., Stevenson, L. W., Dembitsky, W., Long, J. W., Ascheim, D. D., Tierney, A. R., Levitan, R. G., Watson, J. T., Ronan, N. S., Meier, P. (2001). Long-term use of left ventricular assist device for end-stage heart failure. *N Engl J Med* 345(20): 1435-1443.

Sabbah, H., and Sharov, V. (1998). Apoptosis in heart failure. *Prog. Cardiovasc. Dis.* 40: 549-562.

Sadoshima, J., and Izumo, S. (1997). The cellular and molecular response of cardiac myocytes to mechanical stress. *Ann. Rev. Physiol.* 59: 551-571.

SOLVD Investigators (1991). Effect of enalapril on survival in patients with reduced left ventricular ejection fractions and congestive heart failure. *N Engl J Med* 325: 293-302.

Taber L A (2001) Biomechanics of cardiovascular development. *Ann. Rev. Biomed Engr.* 3:1-25.

Torre-Amione, G., Stetson, S. J., Youker, K. A., Durand, J. B., Radovancevic, B., Delgado, R. M., Frazier, O. H., Entman, M. L., Noon, G. P. (1999) Decreased expression of tumor necrosis factor-alpha in failing human myocardium after mechanical circulatory support: A potential mechanism for cardiac recovery. *Circulation* 100: 1189-1193.

Vineberg, A. (1958). Cardiac Resuscitation Device. U.S. Pat. No. 2,826,193.

Weber, K. T., Brilla, C. G., and Janicki, J. S. (1993). Myocardial fibrosis: Functional significance and regulatory factors. *Cardiovasc. Res.* 27: 341-348.

Williams, M. R., Artrip, J. H. (2001). Direct cardiac compression for cardiogenic shock with the CardioSupport System. *Ann Thorac Surg* 71: S188-9.

Wolff, M. R., Buck, S. H., Stoker, S. W., Greater, M. L., Mentzer, R. M. (1996) Myofibrillar calcium sensitivity of isometric tension is increased in human dilated cardiomyopathies: Role of altered beta-adrenergically mediated protein phosphorylation. *J Clin Invest* 98: 167-176.

Zafeiridis, A., Jeevanandam, V., Houser, S. R., Margulies, K. B. (1998) Regression of cellular hypertrophy after left ventricular assist device support. *Circulation* 98: 656-662.

What is claimed is:

1. A contoured heart assist device adapted to surround the heart that reduces dyskinesis and hypokinesis comprising:
   an outer member that surrounds a selectively inflatable end-systolic heart shaped inner bladder, wherein the selectively inflatable end-systolic heart shaped inner bladder comprises at least one heart shaped contoured supports contoured to surround at least a portion of a heart to provide curvatures similar to the proper shape of the heart when pressurized to compress the heart during contraction without inverting or significantly perturbing the curvatures of the heart; and
   one or more fluid connections in communication with the selectively inflatable end-systolic heart shaped inner bladder for pressurization and depressurization.

2. The device of claim 1, wherein the at least one heart shaped contoured supports form one or more inflatable heart shaped compartments having an expanded curvature optimized to fit generally the proper end-systolic shape of the heart.

3. The device of claim 1, wherein the selectively inflatable end-systolic heart shaped inner bladder comprises one or more membranes that are at least partially folded when depressurized and at least partially unfolded when pressurized.

4. The device of claim 1, wherein the selectively inflatable end-systolic heart shaped inner bladder comprises one or more inflatable tapered compartments formed by the at least one heart shaped contoured supports to provide an expanded curvature similar to the proper end-systolic shape of the heart.

5. The device of claim 1, wherein the at least one heart shaped contoured supports comprise one or more wires that form a shape generally appropriate to the proper end-systolic shape of the heart.

6. The device of claim 1, wherein the selectively inflatable end-systolic heart shaped inner bladder comprises a material that is substantially fluid-impermeable and substantially elastic.

7. The device of claim 1, wherein the selectively inflatable end-systolic heart shaped inner bladder is generally collapsible when depressurized.

8. The device of claim 1, wherein the selectively inflatable end-systolic heart shaped inner bladder is reinforced to control expansion during pressurization.

9. The device of claim 1, wherein the selectively inflatable end-systolic heart shaped inner bladder comprises a biocompatible material.

10. The device of claim 1, wherein at least a portion of the selectively inflatable end-systolic heart shaped inner bladder comprises elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated polystyrene-butadiene) copolymer, poly(tetramethylene-ether glycol) urethanes, poly(hexamethylenecarbonate-ethylenecarbonate glycol) urethanes and combinations thereof.

11. The device of claim 1, wherein the selectively inflatable end-systolic heart shaped inner bladder further comprises implanted, coated or disseminatable bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof.

12. The device of claim 1, wherein the one or more fluid connections are connected to a pneumatic pressure source.

13. The device of claim 1, wherein the one or more fluid connections comprise an inlet port and an outlet port wherein the device is inflated with a positive pressure during systole and the device is deflated with a suction during diastole.

14. A heart contoured direct cardiac compression device that applies forces to the exterior, epicardial boundary of the heart to restrict inflow and modulate right flow versus left flow through the heart comprising:
an outer member that surrounds a selectively inflatable end-systolic heart shaped inner bladder, wherein the selectively inflatable end-diastolic heart contoured inner bladder comprises at least one heart shaped contoured supports contoured to compress the heart during contraction without inverting or significantly perturbing the curvatures of the heart, wherein at least a portion of the at least one heart shaped contoured supports protrude inward towards the right ventricle to decrease the end-diastolic volume of the right ventricle during diastole; and
an inlet connection in communication with the selectively inflatable end-diastolic heart shaped contoured inner bladder; and
an outlet connection in communication with the selectively inflatable end-diastolic heart contoured bladder wherein the inlet connection and outlet connection pressurize and depressurize the selectively inflatable end-diastolic heart contoured inner bladder, wherein residual pressure is applied about the right ventricle to not fully deflate during diastole.

15. The device of claim 14 further comprising a pressurization system comprising an inlet line in communication with the inlet connection to operatively expand the selectively inflatable end-diastolic heart contoured inner bladder and an outlet line in communication with the outlet connection to operatively withdraw fluid from the selectively inflatable end-diastolic heart shaped contoured inner bladder.

16. The device of claim 14, wherein the selectively inflatable end-diastolic heart contoured inner bladder comprises one or more membranes that are at least partially folded when depressurized and at least partially unfolded when pressurized.

17. The device of claim 14, wherein the selectively inflatable end-diastolic heart contoured inner bladder comprises a substantially fluid-impermeable and substantially elastic material.

18. The device of claim 14, wherein the selectively inflatable end-diastolic heart shaped inner bladder comprises one or more inflatable tapered compartments formed by the one or more contoured supports to provide an expanded curvature similar to the proper end-diastolic shape of the heart, wherein residual pressure is applied about the right ventricle to not fully deflate during diastole.

19. A direct cardiac compression device that applies forces to the exterior, epicardial boundary of the heart optimized to fit an end-systolic shaped heart geometry comprising:
an outer member that surrounds a selectively inflatable end-systolic heart shaped inner bladder, wherein the selectively inflatable heart shaped inner bladder comprises at least one end-systolic heart shaped inner bladders to compress the heart during contraction without inverting or significantly perturbing the curvatures of the heart
when the pressurizable chamber is pressurized; and
one or more fluid connections in communication with the selectively inflatable bladder to pressurize and depressurize the selectively inflatable bladder.

20. A direct cardiac compression device that promotes a heart shaped contraction strain pattern on a diseased or damaged heart that reduces dyskinetic or hypokinetic motions comprising:
a selectively inflatable end-systolic heart shaped bladder with one or more heart contoured supports configured to surround at least a portion of the heart and contour to the end-systolic shape of the heart when pressurized to compress the heart during contraction without inverting or significantly perturbing the curvatures of the heart; and
one or more fluid connections in communication with the selectively inflatable end-systolic heart shaped bladder for Pressurization and depressurization.

* * * * *